United States Patent
Joshi et al.

(10) Patent No.: US 8,906,953 B2
(45) Date of Patent: Dec. 9, 2014

(54) PYRROLIDINE SUBSTITUTE FLAVONES FOR THE TREATMENT OF INFLAMMATORY DISORDERS

(75) Inventors: Kalpana Sanjay Joshi, Mumbai (IN); Sapna Hasit Parikh, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 150 days.

(21) Appl. No.: 13/580,815

(22) PCT Filed: Feb. 26, 2010

(86) PCT No.: PCT/IB2010/050837
§ 371 (c)(1),
(2), (4) Date: Aug. 23, 2012

(87) PCT Pub. No.: WO2011/104584
PCT Pub. Date: Sep. 1, 2011

(65) Prior Publication Data
US 2012/0316216 A1 Dec. 13, 2012

(51) Int. Cl.
| A61K 31/353 | (2006.01) |
| A61K 31/4025 | (2006.01) |
| A61P 19/02 | (2006.01) |
| C07D 311/32 | (2006.01) |
| C07D 405/04 | (2006.01) |
| C07D 409/04 | (2006.01) |

(52) U.S. Cl.
CPC .......... *C07D 405/04* (2013.01); *A61K 31/4025* (2013.01); *C07D 409/04* (2013.01)
USPC .......... 514/422; 514/456; 548/416; 548/427; 548/429; 548/517; 548/525

(58) Field of Classification Search
CPC . A61K 31/353; A61K 31/4025; C07D 311/32
USPC .......... 514/422, 456; 548/416, 427, 429, 517, 548/525
See application file for complete search history.

(56) References Cited

U.S. PATENT DOCUMENTS

| 4,900,727 A | 2/1990 | Kattige et al. |
| 7,271,193 B2 | 9/2007 | Lal et al. |
| 2004/0106581 A1 | 6/2004 | Lal et al. |
| 2007/0015802 A1 | 1/2007 | Lal et al. |

FOREIGN PATENT DOCUMENTS

WO  2007/148158 A1  12/2007

OTHER PUBLICATIONS

Baker, Wilson, "Molecular Rearrangement of some o-Acyloxyacetophenones and the Mechanism of the Production of 3-Acylchromones", J. Chem. Soc., 1933, pp. 1381-1389.

Brennan, Fionula M., et al., "Inhibitory Effect of TNFα Antibodies on Synovial Cell Interleukin-1 Production in Rheumatoid Arthritis", The Lancet, Jul. 29, 1989, pp. 244-247.

Catrina, Anca Irinel, et al., "Evidence that Anti-Tumor Necrosis Factor Therapy With Both Etanercept and Infliximab Induces Apoptosis in Macrophages, But Not Lymphocytes, in Rheumatoid Arthritis Joints", Arthritis and Rheumatism, vol. 52, No. 1, Jan. 2005, pp. 61-72.

Dhawan, Punita, et al., "Critical role of p42/44$^{MAPK}$ activation in anisomycin and hepatocyte growth factor-induced LDL receptor expression: activation of Raf-1/MEK-1/p42/44$^{MAPK}$ cascade alone is sufficient to induce LDL receptor expression", Journal of Lipid Research, vol. 40, 1989, pp. 1911-1919.

Huang, Zheng, et al., "The next generation of PDE4 inhibitors", Current Opinion in Chemical Biology, 2001, 5, pp. 432-438.

Jansky, L., et al., "Dynamics of Cytokine Production in Human Peripheral Blood Mononuclear Cells Stimulated by LPS or Infected by *Borrelia*", Physiological Research, 2003, 52, pp. 593-598.

Lee, Matthew R., et al., MAP Kinase p38 Inhibitors: Clinical Results and an Intimate Look at Their Interactions with p38α Protein, Current Medicinal Chemistry, 2005, 12, pp. 2979-2994.

Manna, Sunil, K., et al., "Silymarin Suppresses TNF-Induced Activation of NF-kB, c-Jun N-Terminal Kinase, and Apoptosis", J of Immunol, 1999, 163, pp. 6800-6809.

Moreira, A.L., et al., "Thalidomide protects mice against LPS-induced shock", Braz J Med Biol Res 30(10), 1997, pp. 1199-1207.

(Continued)

*Primary Examiner* — Renee Claytor
*Assistant Examiner* — Sahar Javanmard
(74) *Attorney, Agent, or Firm* — Ladas & Parry LLP

(57) ABSTRACT

The present invention relates to the use of a compound of formula 1,

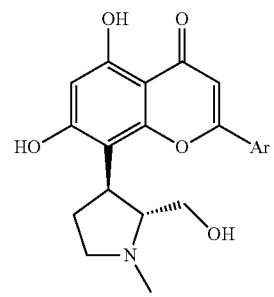

Formula 1 a stereoisomer or a tautomer thereof, or a pharmaceutically acceptable salt or a pharmaceutically acceptable solvate thereof, for the treatment of an inflammatory disorder. The invention further relates to a pharmaceutical composition comprising a compound of formula 1 and at least one pharmaceutically acceptable carrier, for use in the treatment of an inflammatory disorder. The invention also relates to a method for the treatment of an inflammatory disorder by administering a therapeutically effective amount of the compound of formula 1 to a subject in need thereof.

2 Claims, 5 Drawing Sheets

(56) References Cited

OTHER PUBLICATIONS

Rakoff-Nahoum, Seth, "Why Cancer and Inflammation?", Yale Journal of Biology and Medicine 79 (2008), pp. 123-130.

Naik, Ramachandra G., et al., "An Antiinflammatory Cum Immunomodulatory Piperidinylbenzopyranone From Dysoxylum Binectariferum: Isolation, Structure and Total Synthesis", Tetrahedron, 1988, 44(7), pp. 2081-2086.

Rossi, Adriano G., et al., "Cylin-dependent kinase inhibitors enhance the resolution of inflammation by promoting inflammatory cell apoptosis", Nature Medicine, vol. 12, No. 9, Sep. 30, 2006, pp. 1056-1064.

Terato, Kuniaki, et al., "Collagen-Induced Arthritis in Mice", Journal of Experimental Medicine, vol. 162, Aug. 1985, pp. 637-646.

Yamaguchi, Masahiko, et al., "Selective Inhibition of Vascular Cell Adhesion Molecule-1 Expression by Verapamil in Human Vascular Endothelial Cells", Transplantation, vol. 63, No. 5, Mar. 15, 1997, pp. 759-764.

Histopathological evaluation of the compound of example 3

Vehicle control

Enbrel 3mg/kg s.c.

Compound of example 3; 50 mg/kg, p.o.

PYRROLIDINE SUBSTITUTE FLAVONES FOR THE TREATMENT OF INFLAMMATORY DISORDERS

CROSS REFERENCE APPLICATIONS

This application is a 371 of International Application PCT/IB2010/050837 filed 26 Feb. 2010 entitled "Pyrrolidine Substituted Flavones For The Treatment Of Inflammatory Disorders", which was published on 1 Sep. 2011, with International Publication Number WO 2011/104584 A1, the content of which is incorporated herein by reference.

FIELD OF THE INVENTION

The present invention relates to use of the compounds of formula 1 (as described herein), a stereoisomer or a tautomer thereof, or a pharmaceutically acceptable salt or a pharmaceutically acceptable solvate thereof, for the treatment of inflammatory disorders.

BACKGROUND OF THE INVENTION

Inflammation plays a fundamental role in host defenses and the progression of immune-mediated diseases. The inflammatory response is initiated in response to an injury (e.g. trauma, ischemia, and foreign particles) and/or an infection (e.g. bacterial or viral infection) by, including chemical mediators (e.g. cytokines and prostaglandins) and inflammatory cells (e.g. leukocytes). It is characterized by increased blood flow to the tissue, causing pyrexia, erythema, induration and pain.

A delicate well-balanced interplay between the humoral and cellular immune elements in the inflammatory response enables the elimination of harmful agents and the initiation of the repair of damaged tissue. When this delicately balanced interplay is disrupted, the inflammatory response may result in considerable damage to normal tissue and may be more harmful than the original insult that initiated the reaction. In these cases of uncontrolled inflammatory responses, clinical intervention is needed to prevent tissue damage and organ dysfunction. Diseases such as rheumatoid arthritis, osteoarthritis, Crohn's disease, asthma, allergies, septic shock syndrome, atherosclerosis, inflammatory bowel disease among other clinical conditions are characterized by chronic inflammation.

Several proinflammatory cytokines, especially TNF-$\alpha$ (tumor necrosis factor-$\alpha$) and interleukins (IL-1$\beta$, IL-6, IL-8) play an important role in the inflammatory process. Both IL-1 and TNF-$\alpha$ are derived from mononuclear cells and macrophages and in turn induce the expression of a variety of genes that contribute to the inflammatory process.

Rheumatoid arthritis (RA) is an autoimmune disorder. RA is a chronic, systemic, articular inflammatory disease of unknown etiology. In RA, the normally thin synovial lining of joints is replaced by an inflammatory, highly vascularized, invasive fibrocollagenase tissue (pannus), which is destructive to both cartilage and bone. Areas that may be affected include the joints of the hands, wrists, neck, jaw, elbows, feet and ankles. Cartilage destruction in RA is linked to aberrant cytokines and growth factor expression in the affected joints.

Osteoarthritis (OA, also known as degenerative arthritis, degenerative joint disease), is the most common type of arthritis involving degradation of joints, including articular cartilage and the subchondral bone next to it. In OA, a variety of potential forces, hereditary, developmental, metabolic, and mechanical, may initiate processes leading to loss of cartilage, a strong protein matrix that lubricates and cushions the joints. When bone surfaces become less well protected by cartilage, subchondral bone may be exposed and damaged, with regrowth leading to a proliferation of ivory-like, dense, reactive bone in central areas of cartilage loss, a process called eburnation. Due to decreased movement because of the pain, regional muscles may atrophy, and ligaments may become more lax. OA is the most common form of arthritis, and the leading cause of chronic disability.

Inflammatory bowel disease (IBD) is a group of disorders that cause inflammation of the intestines. The inflammation lasts for a long time and usually relapses. The two major types of IBD are Crohn's disease and ulcerative colitis. Crohn's disease occur when the lining and wall of the intestines becomes inflamed resulting in the development of ulcers. Although Crohn's disease can occur in any part of the digestive system, it often occurs in the lower part of the small intestine where it joins the colon. Ulcerative colitis is a chronic auto-immune/inflammatory disease of unknown etiology afflicting the large intestine and affecting millions of people worldwide. It is well-established that a dysfunctional immune-response involving components of normal gastrointestinal gram-negative bacteria and increased expression of pro-inflammatory cytokines, chemokines, endothelial cell adhesion molecules (ECAMs) and enhanced leukocyte infiltration into colonic interstitium, play a key role in the pathogenesis of colitis. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Signs and symptoms of the disease include cramping, lower abdominal pain, rectal bleeding, and frequent, loose discharges consisting mainly of blood, pus, and mucus with scanty fecal particles. A total colectomy may be required for acute, severe or chronic, unremitting ulcerative colitis.

Psoriasis is a chronic, non-contagious autoimmune disease which affects the skin and joints. It commonly causes red scaly patches to appear on the skin. The scaly patches caused by psoriasis, called psoriatic plaques, are areas of inflammation and excessive skin production. Psoriasis can also cause inflammation of the joints, which is known as psoriatic arthritis. Ten to fifteen percent of people with psoriasis have psoriatic arthritis. There are many treatments available, but because of its chronic recurrent nature, psoriasis is difficult to treat.

Tumor Necrosis Factor-$\alpha$ (TNF-$\alpha$), a pleiotropic cytokine, is produced mainly by macrophages, but other types of cells also produce it. TNF-$\alpha$ demonstrates beneficial as well as pathological activities. It has both growth stimulating effects and growth inhibitory properties, besides being self-regulatory. The beneficial functions of TNF-$\alpha$ include maintaining homeostasis by regulating the body's circadian rhythm, mounting an immune response to bacterial, viral, fungal and parasitic infections, replacing or remodeling injured tissue by stimulating fibroblast growth and, as the name suggests, killing certain tumors. TNF-$\alpha$ is derived from mononuclear cells and macrophages and in turn induces the expression of a variety of genes that contribute to various disorders such as inflammatory disorders.

Although TNF-$\alpha$ plays a critical role in innate and acquired immune responses, inappropriate production of TNF-$\alpha$ produce pathological changes resulting in chronic inflammation and tissue damage. TNF-$\alpha$ has been shown to play a crucial role in the pathogenesis of many chronic inflammatory diseases such as inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, vasculitis, ulcerative colitis, psoriasis, adult respiratory distress syndrome, diabetes, skin delayed type hypersensitivity disorders and Alzheimer's disease.

IL-1 (Interleukin 1) is an important part of the innate immune system, which regulates functions of the adaptive immune system. The balance between IL-1 and IL-1 receptor antagonist (IL-1ra) in local tissues influences the possible development of an inflammatory disease and resultant structural damage. In the presence of an excess amount of IL-1, inflammatory and autoimmune disorders may be developed in joints, lungs, gastrointestinal tract, central nervous system (CNS) or blood vessels.

Cellular adhesion molecules intercellular adhesion molecule1 (ICAM-1), vascular-cell adhesion molecule1 (VCAM-1), and E-Selectin are responsible for the recruitment of inflammatory cells, such as neutrophils, eosinophils, and T lymphocytes, from the circulation to the site of inflammation. The recruitment and retention of leukocyte is a critical event in the pathogenesis of all chronic inflammatory diseases such as RA.

The first line of treatment for inflammatory disorders involves the use of non-steroidal anti-inflammatory drugs (NSAIDs) e.g. ibuprofen, naproxen to alleviate symptoms such as pain. However, despite the widespread use of NSAIDs, many individuals cannot tolerate the doses necessary to treat the disorder over a prolonged period of time as NSAIDs are known to cause gastric erosions. Moreover, NSAIDs merely treat the symptoms of the inflammatory disorder and not the cause. When patients fail to respond to NSAIDs, other drugs such as methotrexate, gold salts, D-penicillamine and corticosteroids are used. These drugs also have significant side effects.

Monoclonal antibody drugs such as Infliximab, Etanercept and Adalimumab are useful as anti-inflammatory agents, but have drawbacks such as route of administration (only parenteral), high cost, allergy induction, activation of latent tuberculosis, increased risk of cancer and congestive heart disease.

Although phosphodiesterase-4 (PDE4) inhibitors have been developed for the treatment of asthma, atopic dermatitis, rheumatoid arthritis, multiple sclerosis, and Crohn's disease, the non-selective inhibition of multiple PDE4s leads to complex physiological responses. The therapeutic potential of PDE4 inhibitors has been hampered by their dose-limiting side effects of nausea and emesis as in the case of Cilomilast (SB 207499, Ariflo™) (Current Opinion in Chemical Biology, 2001, 5, 432-438).

Similarly, although p38 mitogen-activated protein kinase (MAPK) inhibitors are potential anti-inflammatory agents, the side-effects associated with their use include gastric ulcerations, hepatotoxicity, and nephrotoxicity. For instance, development of 2-[2(S)-Amino-3-phenylpropylamino]-3-methyl-5-(2-naphthyl)-6-(4-pyridyl)pyrimidin-4(3H)-one (AMG 548, Amgen) was suspended due to random liver enzyme elevations that were not dose or exposure dependent. The impact on safety profiles after chronic treatment using p38 MAP kinase inhibitors, needs to be established (Current Medicinal Chemistry, 2005, 12, 2979-2994).

U.S. Pat. No. 4,900,727 discloses benzopyran-4-one derivatives as antiinflammatory agents. Anti-inflammatory benzopyran-4-one derivative from *Dysoxylum binectariferum* is described by R. G. Naik et al in Tetrahedron, 1988, 44 (7), 2081-2086.

Notwithstanding the availability of a number of therapies for the treatment of inflammatory disorders, there still exists a continuing need for improved and alternative medicaments for the treatment of inflammatory disorders.

U.S. Pat. No. 7,271,193, Published US application US20070015802, and published PCT application, WO2007148158, all of which are incorporated herewith in all entirety as references, describe pyrrolidine substituted flavones as CDK inhibitors with utility in the treatment of different types of cancers. The present inventors have found that the pyrrolidine substituted flavones designated herein as compounds of formula 1 find use in the treatment of inflammatory disorders. The scope of the present invention is to provide a new anti-inflammatory use of the above-mentioned pyrrolidine substituted flavones.

SUMMARY OF THE INVENTION

According to one aspect of the present invention, there is provided use of a compound of formula 1 (structure as indicated herein below), a stereoisomer or a tautomer thereof or a pharmaceutically acceptable salt or a pharmaceutically acceptable solvate thereof, for the treatment of an inflammatory disorder.

According to a further aspect of the present invention, there is provided a pharmaceutical composition comprising the compound of formula 1, a stereoisomer or a tautomer thereof or a pharmaceutically acceptable salt, or a pharmaceutically acceptable solvate thereof and at least one pharmaceutically acceptable carrier, for use in the treatment of an inflammatory disorder.

The present invention also provides a method for the treatment of an inflammatory disorder, comprising administering to a subject in need thereof, a therapeutically effective amount of a compound of formula 1, a stereoisomer or a tautomer thereof; or a pharmaceutically acceptable salt or a pharmaceutically acceptable solvate thereof.

The present invention in a further aspect concerns use of the compounds of formula 1 or a stereoisomer or a tautomer thereof or a pharmaceutically acceptable salt or a pharmaceutically acceptable solvate thereof, for the manufacture of a medicament for the treatment of an inflammatory disorder.

According to another aspect of the present invention, there is provided use of a compound of formula 1 (as described herein) or a stereoisomer, or a tautomer thereof or a pharmaceutically acceptable salt, or a pharmaceutically acceptable solvate thereof, for the treatment of an inflammatory disorder mediated by elevated levels of one or more inflammatory cytokines such as Tumor Necrosis Factor-alpha (TNF-α) and interleukins (IL-1β, IL-6, IL-8) or increased expression of one or more cell adhesion molecules such as intercellular adhesion molecule1 (ICAM-1), vascular-cell adhesion molecule1 (VCAM-1) and E-Selectin or a combination thereof.

DETAILED DESCRIPTION OF THE INVENTION

Figure 1:
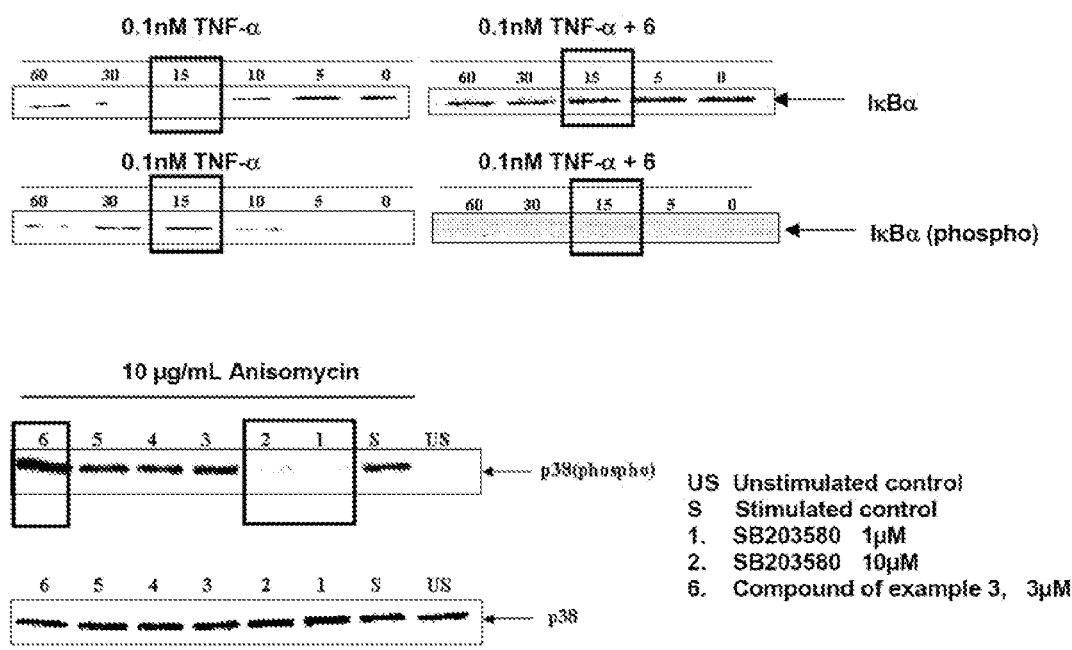
FIG. 1 shows western blot analysis for in vitro screening for p38 MAP Kinase inhibition and IκBα degradation

In an embodiment, the present invention relates to the use of a compound of formula 1:

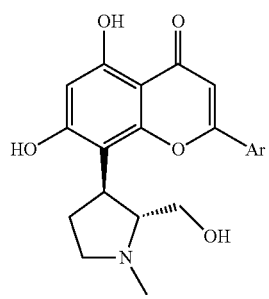

Formula 1 wherein Ar is a phenyl or a heteroaryl ring, wherein the phenyl or the heteroaryl ring may be unsubstituted or substituted by 1, 2, or 3 identical or different substituents selected from: halogen, nitro, cyano, $C_1$-$C_4$-alkyl, fluoromethyl, difluoromethyl, trifluoromethyl, hydroxy, $C_1$-$C_4$-alkoxy, carboxy, $C_1$-$C_4$-alkoxycarbonyl, $C_1$-$C_4$-alkylenehydroxyl, $CONH_2$, $CONR_1R_2$, $SO_2NR_1R_2$, cycloalkyl, $N_1R_1R_2$ and $SR_3$;

wherein $R_1$ and $R_2$ are each independently selected from: hydrogen, $C_1$-$C_4$-alkyl, $C_1$-$C_4$-aralkylcarbonyl and aryl, or $R_1$ and $R_2$, together with the nitrogen atom to which they are bonded, form a 5- or 6-membered ring, which may optionally contain at least one additional heteroatom; and $R_3$ is selected from hydrogen, $C_1$-$C_4$-alkyl, and phenyl; or a stereoisomer or a tautomer thereof or a pharmaceutically acceptable salt or a pharmaceutically acceptable solvate thereof; in the treatment of an inflammatory disorder.

DEFINITIONS

For the purpose of the disclosure, listed below are definitions of various terms used to describe the present invention. These definitions apply to the terms as they are used throughout the specification and the appended claims (unless they are otherwise limited in specific instances) either individually or as part of a larger group. They should not be interpreted in the literal sense. They are not general definitions and are relevant only for this application.

The term "alkyl" refers to the radical of saturated aliphatic groups, including straight-chain alkyl groups and branched-chain alkyl groups. Examples of alkyl residues containing from 1 to 4 carbon atoms are: methyl, ethyl, n-propyl, n-butyl, isopropyl, isobutyl, sec-butyl, and t-butyl.

The term "cycloalkyl" refers to a non-aromatic mono or multicyclic ring system of about 3 to 7 carbon atoms. Examples of cycloalkyl groups include cyclopropyl, cyclobutyl, cyclopentyl, cyclohexyl and the like. The cycloalkyl groups may be unsubstituted or substituted by one or more different substituents selected from: halogen, nitro, cyano, $C_1$-$C_4$-alkyl, fluoromethyl, difluoromethyl, trifluoromethyl, hydroxy, $C_1$-$C_4$-alkoxy, carboxy, $C_1$-$C_4$-alkoxycarbonyl, and $CONH_2$.

The term "alkoxy" as used herein refers to an alkyl group, as defined above, having an oxygen radical attached thereto. Representative alkoxy groups include methoxy, ethoxy, propoxy, t-butoxy and the like.

The term "halogen" refers to chlorine, bromine, fluorine and iodine.

The term "heteroaryl" as used herein refers to a monocyclic aromatic ring system containing 1 to 3 identical or different heteroatoms. The term "heteroatom" refers to nitrogen, oxygen and sulphur. The heteroaryl group can, for example, have 1 or 2 sulphur atoms, 1 or 2 oxygen atoms and/or 1 to 3 nitrogen atoms in the ring. In monocyclic groups, heteroaryl can be a 3-membered, 4-membered, 5-membered or 6-membered. Heteroaryl groups include pyrrole, thiophene, oxazole, furan, thiazole, pyrrazole, pyridine and the like.

In the specification where the term "compound of formula 1" is used alone, wherever appropriate, it is deemed to include a stereoisomer, or a tautomer or a pharmaceutically acceptable salt, or a pharmaceutically acceptable solvate of the compound of the formula 1.

It will be understood that "substitution" or "substituted with" includes the implicit proviso that such substitution is in accordance with permitted valence of the substituted atom and the substituents, as well as represents a stable compound, which does not readily undergo undesired transformation such as by rearrangement, cyclization, or elimination.

The term "pharmaceutically acceptable" means that the carrier, diluent, excipients, and/or salt must be compatible with the other ingredients of the formulation, and not deleterious to the recipient thereof.

The term, "therapeutically effective amount" as used herein means an amount of the compound of formula 1 or a composition comprising said compound, sufficient to significantly induce a positive modification in the condition to be regulated or treated, but low enough to avoid side effects if any (at a reasonable benefit/risk ratio), within the scope of sound medical judgment. The therapeutically effective amount of the compound of formula 1 or the composition containing said compound will vary with the particular inflammatory disorder being treated, the age and physical condition of the subject (patient), the severity of the condition being treated/prevented, the duration of the treatment, the nature of concurrent therapy, the specific compound or composition employed, the particular pharmaceutically acceptable carrier utilized, and like factors.

The term 'treating", "treat" or "treatment" as used herein refers to alleviate, slow the progression, attenuation or cure of existing disease (for example, rheumatoid arthritis)

The term "subject" as used herein refers to an animal, preferably a mammal, and most preferably a human.

The term "inflammatory disorder" as used herein refers to a disease or a condition characterized by chronic inflammation including but not limited to rheumatoid arthritis, osteoarthritis, juvenile rheumatoid arthritis, psoriatic arthritis, refractory rheumatoid arthritis, chronic non-rheumatoid arthritis, osteoporosis/bone resorption, coronary heart disease, atherosclerosis, vasculitis, ulcerative colitis, psoriasis, Crohn's disease, adult respiratory distress syndrome, delayed-type hypersensitivity in skin disorders, septic shock syndrome, and inflammatory bowel disease.

The term "pharmaceutically acceptable salt(s)" is meant to include salt(s) of the active compounds i.e. the compounds of formula 1, which are prepared with acids or bases, depending on the particular substituents found on the compounds described herein. Examples of pharmaceutically acceptable base addition salts include sodium, potassium, calcium, magnesium, ammonium or organic base salt. Examples of pharmaceutically acceptable organic base addition salts include those derived from organic bases like lysine, arginine, guanidine, diethanolamine and the like. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogen phosphoric, sulfuric, monohydrogensulfuric, hydriodic, or phosphorous acids and the like, as well as the salts derived from organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, glucuronic or galacturonic acids and the like. The neutral forms of the compounds may be regenerated by contacting the salt with a base or acid and isolating the parent compound in the conventional manner.

The term "pharmaceutically acceptable carrier" as used herein means a diluent, encapsulating material or formulation auxiliary, which is non-toxic, inert, solid, or semi-solid. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt, gelatin; talc, as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

The compounds of formula I may be prepared according to the methods disclosed in U.S. Pat. No. 7,271,193, US Patent Publ. 20070015802 and PCT Patent Publication No. WO2007148158, which are incorporated herein by reference. The method described in the following Scheme I can be used to prepare intermediate of formula (VIA).

SCHEME 1

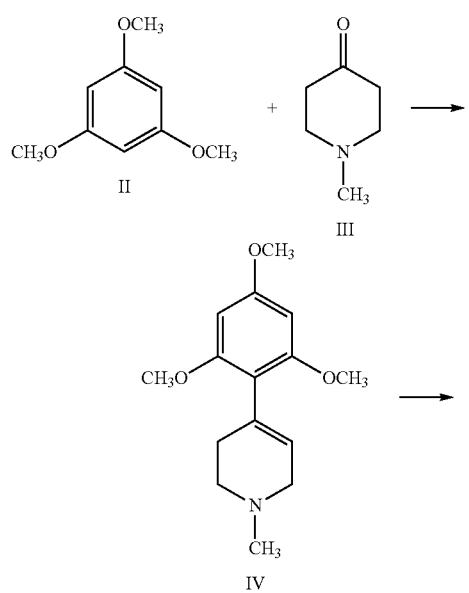

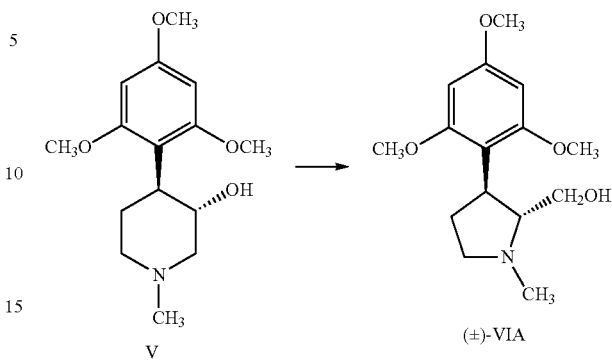

The preparation steps up to the compound of formula V starting from the compound of formula (II) are described in U.S. Pat. No. 4,900,727, which is incorporated herein by reference. 1-Methyl-4-piperidone (compound of formula III) was reacted with a solution of 1,3,5-trimethoxybenzene (compound of formula II) in glacial acetic acid, to yield 1-methyl-4-(2,4,6-trimethoxyphenyl)-1,2,3,6-tetrahydropyridine (compound of formula IV). Compound of formula IV is reacted with boron trifluoride diethyl etherate, sodium borohydride and tetrahydrofuran to obtain compound of formula V. In the conversion of the compound of formula V to that of formula VIA in the above scheme, the hydroxyl function on the piperidine ring may be converted to a leaving group such as tosyl, mesyl, triflate or halide by treatment with an appropriate reagent such as p-toluenesulfonylchloride, methanesulfonylchloride, triflic anhydride or phosphorous pentachloride in the presence of oxygen nucleophiles such as triethylamine, pyridine, potassium carbonate or sodium carbonate, followed by ring contraction in the presence of oxygen nucleophiles such as sodium acetate or potassium acetate in an alcoholic solvent such as isopropanol, ethanol or propanol. The ring contraction involved in this step may be effected before flavone formation as depicted in the above scheme or it may be done after building the flavone with the desired substitutions.

Enantiomerically pure (−)-trans enantiomer of an intermediate compound of the formula VIA as defined, is used for the preparation of an enantiomerically pure compound of the formula I as defined. By using an intermediate having a high enantiomeric purity as a starting compound in the process, the resultant (+)-trans enantiomer of pyrrolidines substituted with flavone represented by formula I produced by the process has a correspondingly high enantiomeric purity.

The process for the preparation of an enantiomerically pure (+)-trans enantiomer of a compound of formula I, or a pharmaceutically acceptable salt thereof, from the resolved enantiomerically pure (−)-trans enantiomer of the intermediate compound of formula VIA comprises following steps:

(a) treating the resolved enantiomerically pure (−)-trans enantiomer of the intermediate compound of formula VIA,

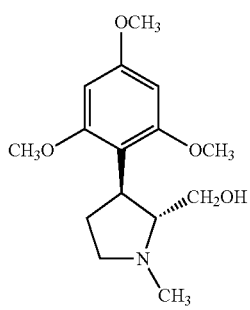

VIA with acetic anhydride in the presence of a Lewis acid catalyst to obtain a resolved acetylated compound of formula VIIA,

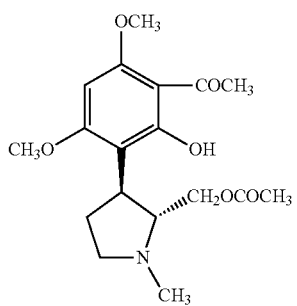

VIIA (b) reacting the resolved acetylated compound of formula VIIA with an acid of formula ArCOOH or an acid chloride of formula ArCOCl or an acid anhydride of formula (ArCO)$_2$O or an ester of formula ArCOOCH$_3$, wherein Ar is as defined hereinabove, in the presence of a base and a solvent to obtain a resolved compound of formula VIIIA;

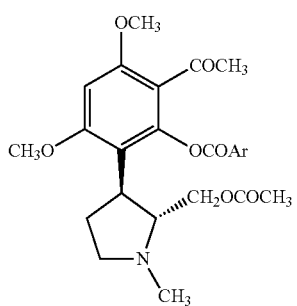

VIIIA (c) treating the resolved compound of formula VIIIA with a base in a suitable solvent to obtain the corresponding resolved β-diketone compound of formula IXA;

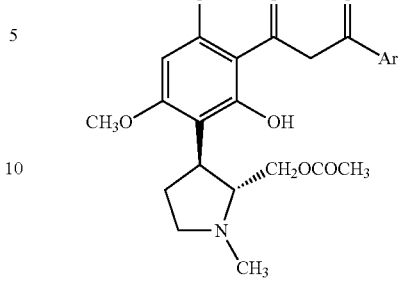

IXA where Ar is as defined.

(d) treating the resolved β-diketone compound of formula IXA with an acid such as hydrochloric acid to obtain the corresponding cyclized compound of formula XA,

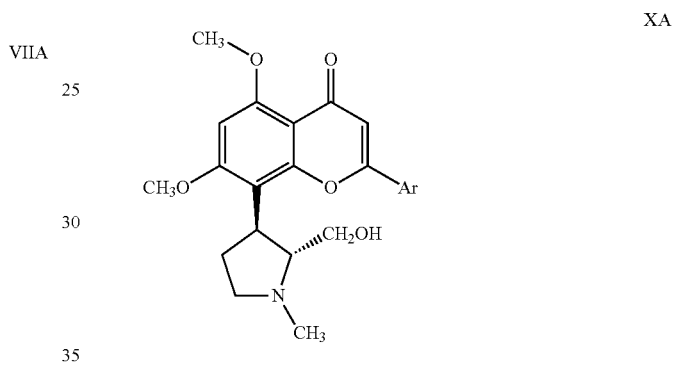

XA (e) subjecting the compound of formula XA to dealkylation by heating it with a dealkylating agent at a temperature ranging from 120-180° C. to obtain the (+)-trans enantiomer of the compound of formula I and, optionally, converting the subject compound into its pharmaceutically acceptable salt.

The Lewis acid catalyst utilized in the step (a) above may be selected from: BF$_3$. Et$_2$O, zinc chloride, aluminium chloride and titanium chloride.

The base utilized in the process step (b) may be selected from triethylamine, pyridine and a DCC-DMAP combination (combination of N,N'-dicyclohexyl carbodiimide and 4-dimethylaminopyridine).

It will be apparent to those skilled in the art, the rearrangement of the compound of formula VIIIA to the corresponding β-diketone compound of formula IXA is known as a Baker-Venkataraman rearrangement (J. Chem. Soc., 1381 (1933) and Curr. Sci., 4, 214 (1933)).

The base used in the process step (c) may be selected from: lithium hexamethyl disilazide, sodium hexamethyldisilazide, potassium hexamethyldisilazide, sodium hydride and potassium hydride. Most preferred base is lithium hexamethyl disilazide.

The dealkylating agent used in process step (e) for the dealkylation of the compound of formula IXA may be selected from: pyridine hydrochloride, boron tribromide, boron trifluoride etherate and aluminium trichloride. Most preferred dealkylating agent is pyridine hydrochloride.

In an aspect of the invention, the compound of formula 1 is selected from the compounds wherein:

Ar is a phenyl ring, wherein the phenyl ring may be unsubstituted or substituted with 1, 2, or 3 identical or different substituents selected from: halogen, nitro, cyano, $C_1$-$C_4$-alkyl, fluoromethyl, difluoromethyl, trifluoromethyl, hydroxy, $C_1$-$C_4$-alkoxy, carboxy and $NR_1R_2$; wherein $R_1$ and $R_2$ are each independently selected from: hydrogen, $C_1$-$C_4$-alkyl and $C_1$-$C_4$-alkylcarbonyl or a stereoisomer or a tautomer thereof or a pharmaceutically acceptable salt or a pharmaceutically acceptable solvate thereof.

In another aspect of the invention, the compound of formula 1 is selected from the compounds wherein:

Ar is a phenyl ring, wherein the phenyl ring may be unsubstituted or substituted with 1, 2, or 3 identical or different substituents selected from: halogen, nitro, cyano, $C_1$-$C_4$-alkyl, fluoromethyl, difluoromethyl and trifluoromethyl; or a stereoisomer or a tautomer thereof or a pharmaceutically acceptable salt or a pharmaceutically acceptable solvate thereof.

In a further aspect of the invention, the compound of formula 1 is selected from:

(+)-trans-2-(2-Chloro-4-trifluoromethyl-phenyl)-5,7-dihydroxy-8-(2-hydroxymethyl-1-methyl-pyrrolidin-3-yl)-chromen-4-one hydrochloride;

(+)-trans-2-(2-Chloro-4-nitro-phenyl)-5,7-dihydroxy-8-(2-hydroxymethyl-1-methyl-pyrrolidin-3-yl)-chromen-4-one hydrochloride;

(+)-trans-2-(2-Chloro-phenyl)-5,7-dihydroxy-8-(2-hydroxymethyl-1-methyl-pyrrolidin-3-yl)-chromen-4-one hydrochloride;

(+)-trans-2-(2-Bromo-5-fluoro-phenyl)-5,7-dihydroxy-8-(2-hydroxymethyl-1-methyl-pyrrolidin-3-yl)-chromen-4-one hydrochloride;

(+)-trans-2-(2-Bromo-5-fluoro-phenyl)-5,7-dihydroxy-8-(2-hydroxymethyl-1-methyl-pyrrolidin-3-yl)-chromen-4-one methane sulfonate;

(+)-trans-2-(2-Chloro-4-cyano-phenyl)-5,7-dihydroxy-8-(2-hydroxymethyl-1-methyl-pyrrolidin-3-yl)-chromen-4-one hydrochloride;

(+)-trans-2-(4-Bromo-2-chloro-phenyl)-5,7-dihydroxy-8-(2-hydroxymethyl-1-methyl-pyrrolidin-3-yl)-chromen-4-one hydrochloride;

(+)-trans-2-(2-Bromo-4-nitro-phenyl)-5,7-dihydroxy-8-(2-hydroxymethyl-1-methyl-pyrrolidin-3-yl)-chromen-4-one hydrochloride;

(+)-trans-2-(2,4-Dichloro-phenyl)-5,7-dihydroxy-8-(2-hydroxymethyl-1-methyl-pyrrolidin-3-yl)-chromen-4-one hydrochloride;

(+)-trans-2-(2-Chloro-5-fluoro-phenyl)-5,7-dihydroxy-8-(2-hydroxymethyl-1-methyl-pyrrolidin-3-yl)-chromen-4-one hydrochloride;

(+)-trans-5,7-Dihydroxy-8-(2-hydroxymethyl-1-methyl-pyrrolidin-3-yl)-2-thiophen-2-yl-chromen-4-one hydrochloride;

(+)-trans-5,7-dihydroxy-8-(2-hydroxymethyl-1-methyl-pyrrolidin-3-yl)-2-(3-nitrophenyl)-chromen-4-one hydrochloride;

(+)-trans-2-(3-Bromo-2-chloro-phenyl)-5,7-dihydroxy-8-(2-hydroxymethyl-1-methyl-pyrrolidin-3-yl)-chromen-4-one hydrochloride;

(+)-trans-2-(3-Chloro-phenyl)-5,7-dihydroxy-8-(2-hydroxymethyl-1-methyl-pyrrolidin-3-yl)-chromen-4-one hydrochloride;

(+)-trans-2-(2-Chloro-3-nitro-phenyl)-5,7-dihydroxy-8-(2-hydroxymethyl-1-methyl-pyrrolidin-3-yl)-chromen-4-one hydrochloride;

(+)-trans-2-(2-Chloro-3-trifluoromethyl-phenyl)-5,7-dihydroxy-8-(2-hydroxymethyl-1-methyl-pyrrolidin-3-yl)-chromen-4-one hydrochloride;

(+)-trans-2-(2-Chloro-3-methyl-phenyl)-5,7-dihydroxy-8-(2-hydroxymethyl-1-methyl-pyrrolidin-3-yl)-chromen-4-one hydrochloride;

(+)-trans-2-(2-Chloro-3-pyrrolidin-1-yl-phenyl)-5,7-dihydroxy-8-(2-hydroxymethyl-1-methyl-pyrrolidin-3-yl)-chromen-4-one hydrochloride;

(+)-trans-2-(3-Bromo-phenyl)-8-(2-hydroxymethyl-1-methyl-pyrrolidin-3-yl)-5,7-dihydroxy-chromen-4-one hydrochloride;

(+)-trans-2-(2,3-Dichloro-phenyl)-5,7-dihydroxy-8-(2-hydroxymethyl-1-methyl-pyrrolidin-3-yl)-chromen-4-one hydrochloride;

(+)-trans-2-(2-Chloro-3-iodo-phenyl)-5,7-dihydroxy-8-(2-hydroxymethyl-1-methyl-pyrrolidin-3-yl)-chromen-4-one hydrochloride;

(+)-trans-2-(2-Chloro-3-isopropylamino-phenyl)-5,7-dihydroxy-8-(2-hydroxymethyl-1-methyl-pyrrolidin-3-yl)-chromen-4-one hydrochloride; and (+)-trans-2-(3-Iodo-phenyl)-5,7-dihydroxy-8-(2-hydroxymethyl-1-methyl-pyrrolidin-3-yl)-chromen-4-one hydrochloride.

In yet another further aspect of the invention, the compound of formula 1 is selected from:

(+)-trans-2-(2-Chloro-4-trifluoromethyl-phenyl)-5,7-dihydroxy-8-(2-hydroxymethyl-1-methyl-pyrrolidin-3-yl)-chromen-4-one hydrochloride;

(+)-trans-2-(2-Chloro-4-nitro-phenyl)-5,7-dihydroxy-8-(2-hydroxymethyl-1-methyl-pyrrolidin-3-yl)-chromen-4-one hydrochloride;

(+)-trans-2-(2-Chloro-phenyl)-5,7-dihydroxy-8-(2-hydroxymethyl-1-methyl-pyrrolidin-3-yl)-chromen-4-one hydrochloride;

(+)-trans-2-(2-Bromo-5-fluoro-phenyl)-5,7-dihydroxy-8-(2-hydroxymethyl-1-methyl-pyrrolidin-3-yl)-chromen-4-one hydrochloride;

(+)-trans-2-(2-Chloro-4-cyano-phenyl)-5,7-dihydroxy-8-(2-hydroxymethyl-1-methyl-pyrrolidin-3-yl)-chromen-4-one hydrochloride;

(+)-trans-2-(2-Bromo-4-nitro-phenyl)-5,7-dihydroxy-8-(2-hydroxymethyl-1-methyl-pyrrolidin-3-yl)-chromen-4-one hydrochloride;

(+)-trans-2-(2,4-Dichloro-phenyl)-5,7-dihydroxy-8-(2-hydroxymethyl-1-methyl-pyrrolidin-3-yl)-chromen-4-one hydrochloride;

(+)-trans-2-(2-Chloro-5-fluoro-phenyl)-5,7-dihydroxy-8-(2-hydroxymethyl-1-methyl-pyrrolidin-3-yl)-chromen-4-one hydrochloride;

(+)-trans-5,7-dihydroxy-8-(2-hydroxymethyl-1-methyl-pyrrolidin-3-yl)-2-(3-nitrophenyl)-chromen-4-one hydrochloride;

(+)-trans-2-(2-Chloro-3-nitro-phenyl)-5,7-dihydroxy-8-(2-hydroxymethyl-1-methyl-pyrrolidin-3-yl)-chromen-4-one hydrochloride;

(+)-trans-2-(2-Chloro-3-methyl-phenyl)-5,7-dihydroxy-8-(2-hydroxymethyl-1-methyl-pyrrolidin-3-yl)-chromen-4-one hydrochloride;

(+)-trans-2-(2,3-Dichloro-phenyl)-5,7-dihydroxy-8-(2-hydroxymethyl-1-methyl-pyrrolidin-3-yl)-chromen-4-one hydrochloride;

(+)-trans-2-(2-Chloro-3-iodo-phenyl)-5,7-dihydroxy-8-(2-hydroxymethyl-1-methyl-pyrrolidin-3-yl)-chromen-4-one hydrochloride; and (+)-trans-2-(2-Chloro-3-isopropylamino-phenyl)-5,7-dihydroxy-8-(2-hydroxy methyl-1-methyl-pyrrolidin-3-yl)-chromen-4-one hydrochloride.

In an embodiment, the present invention is directed to a method for the treatment of an inflammatory disorder, involving administering a therapeutically effective amount of a compound of formula 1 to a subject in need thereof.

In accordance with the present invention, the inflammatory disorders include the disorders which are mediated by elevated levels of one or more inflammatory cytokines (TNF-α, IL-1β, IL-6, IL-8) or increased expression of one or more cell adhesion molecules (ICAM-1, VCAM-1, E-Selectin) or a combination thereof.

In another further embodiment of the invention, the compounds of formula 1 are TNF-α inhibitors and find use in the treatment of disorders associated with abnormal TNF-α activity, including: inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, atherosclerosis, septic shock syndrome, coronary heart disease, vasculitis, ulcerative colitis, psoriasis, adult respiratory distress syndrome, and delayed type hypersensitivity in skin disorders.

In another embodiment of the invention, the compounds of formula 1 are IL-1β, IL-6, and/or IL-8 inhibitors and find use in the treatment of disorders associated with abnormal IL-1β, IL-6, and/or IL-8 activity, including: rheumatoid arthritis, osteoarthritis and other autoimmune conditions such as multiple sclerosis and various forms of lupus.

In yet another embodiment of the invention, the compounds of formula 1 are inhibitors of the expression of one or more cell adhesion molecules such as ICAM-1, VCAM-1, and E-Selectin and find use in the treatment of inflammatory disorders associated with increased expression of cell adhesion molecules.

In an embodiment of the invention, there is provided a pharmaceutical composition comprising a therapeutically effective amount of a compound of formula 1 as an active ingredient and at least one pharmaceutically acceptable carrier, wherein the pharmaceutical composition is adapted for the treatment of an inflammatory disorder.

It is currently contemplated that different pharmaceutical compositions adapted for the treatment of an inflammatory disorder shall contain about 1 to 99%, for example, about 5 to 70%, or about 10 to 30% by weight of the compound(s) of formula 1 or the corresponding weight of their pharmaceutically acceptable salts.

According to the present invention, the pharmaceutically acceptable carrier contained in the pharmaceutical composition may be selected with regard to the intended route of administration of the compounds of formula 1 and standard pharmaceutical practice.

According to the present invention, the pharmaceutical composition can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or ointments, or transdermally in the form of patches, or in other ways, for example in the form of aerosols or nasal sprays.

The pharmaceutical compositions according to the present invention are prepared in a manner known per se and familiar to one skilled in the art e.g., by means of conventional mixing, dissolving, granulating, dragee-making, levigating, emulsifying, encapsulating, entrapping or tabletting processes.

For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, waxes, natural or hardened oils, etc. Suitable carriers for the production of solutions, for example injectable sterile solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

In addition to the compound of formula 1 and the pharmaceutically acceptable carriers, the pharmaceutical compositions can also contain additives such as, for example, fillers, antioxidants, dispersants, emulsifiers, defoamers, flavors, preservatives, solubilizers or colorants.

The dose of the compounds of this invention, which is to be administered, can cover a wide range. The dose to be administered daily is to be selected to suit the desired effect. A dosage of about 1 to 500 mg/m$^2$ of the compound of the present invention may be administered per day. If required, higher or lower daily doses can also be administered. The selected dosage level will depend upon a variety of factors including the activity of the particular compound of formula 1 employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the subject (patient) being treated, and like factors well known in the medical arts.

The present invention also envisages the use of a compound of formula 1 in combination with other pharmaceutically active compounds. For instance, a pharmaceutical composition, including a compound of the formula 1 can be administered to a subject, in particular a human, with another pharmaceutically active compound known to be useful in treating an inflammatory disorder such as NSAIDs, gold sodium thiomalate (GST), methotrexate (MTX), and dexamethasone (DEX) in the form of pharmaceutical preparations.

In accordance with the present invention, certain compounds of formula 1 can exist in unsolvated forms as well as solvated forms, including hydrated forms. Certain compounds of formula 1 may exist in multiple crystalline or amorphous forms. In general, all physical forms are equivalent for the uses contemplated by the present invention and are intended to be within the scope of the present invention.

Those skilled in the art will recognize that stereocentres exist in compounds of formula 1. Accordingly, the present invention includes all possible stereoisomers and geometric isomers of formula 1 and includes not only racemic compounds but also the optically active isomers as well. When a compound of formula 1 is desired as a single enantiomer, it may be obtained either by resolution of the final product or by stereospecific synthesis from either isomerically pure starting material or intermediate. Resolution of the final product, an intermediate or a starting material may be effected by any suitable method known in the art for example *Chiral reagents for Asymmetric Synthesis* by Leo A. Paquette; John Wiley & Sons Ltd (2003). Additionally, in situations wherein tautomers of the compounds of formula 1 are possible, the present invention is intended to include all tautomeric forms of the compounds.

It is understood that modifications that do not substantially affect the various embodiments of this invention are included within the invention disclosed herein.

The compounds of this invention can be prepared by standard organic chemistry as illustrated by the accompanying working examples. The following examples are set forth to illustrate the synthesis of some particular compounds of the present invention and to exemplify general processes. The invention is explained in detail in the examples given below and should not be construed to limit the scope of the invention.

The following abbreviations or terms are used herein:
CD$_3$OD: Deuterated methanol
CDCl$_3$: Deuterated chloroform
DCM: Dichloromethane
DMF: N,N-Dimethylformamide
DMSO: Dimethylsulfoxide
DMSO-d$_6$: Deuterated dimethylsulfoxide
EDTA: Ethylene diamine tetra acetic acid
FCS: Fetal calf serum
HCl: Hydrochloric acid
NaHCO$_3$: Sodium bicarbonate
Na$_2$CO$_3$: Sodium carbonate
NaH: Sodium hydride
n-BuLi: n-butyl Lithium
NMR: Nuclear Magnetic Resonance
PBS: Phosphate buffered saline
THF: Tetrahydrofuran

EXAMPLES

The compounds corresponding to examples 1-22 have been prepared by the method as disclosed in published US application US20070015802, and/or published PCT application, WO2007148158, both of which are incorporated herewith in all entirety as reference.

Example 1

(−)-trans-(3-(3-acetyl-2-hydroxy-4,6-dimethoxyphenyl)-1-methylpyrrolidin-2-yl)methyl acetate The compound was prepared by the method disclosed in example 11 of published US application US20070015802, and example 6 of published PCT application, WO2007148158.

Example 2

(+)-trans-2-(2-Chloro-4-trifluoromethyl-phenyl)-5,7-dihydroxy-8-(2-hydroxy-methyl-1-methylpyrrolidin-3-yl)-chromen-4-one The compound was prepared by the method as disclosed in example 43 of published PCT application, WO2007148158.

Example 3

(+)-trans-2-(2-Chloro-4-trifluoromethyl-phenyl)-5,7-dihydroxy-8-(2-hydroxymethyl-1-methyl-pyrrolidin-3-yl)-chromen-4-one hydrochloride The compound was prepared by the method as disclosed in example 44 of published PCT application, WO2007148158.

Example 4

(+)-trans-2-(2-Chloro-4-nitro-phenyl)-5,7-dihydroxy-8-(2-hydroxymethyl-1-methyl-pyrrolidin-3-yl)-chromen-4-one The compound was prepared by the method as disclosed in example 49 of published PCT application, WO2007148158.

Example 5

(+)-trans-2-(2-Chloro-4-nitro-phenyl)-5,7-dihydroxy-8-(2-hydroxymethyl-1-methyl-pyrrolidin-3-yl)-chromen-4-one hydrochloride The compound was prepared by the method as disclosed in example 50 of published PCT application, WO2007148158.

Example 6

(+)-trans-2-(2-Chloro-phenyl)-5,7-dihydroxy-8-(2-hydroxymethyl-1-methyl-pyrrolidin-3-yl)-chromen-4-one The compound was prepared by the method as disclosed in example 14 of published US application US20070015802, and example 9 of published PCT application, WO2007148158.

Example 7

(+)-trans-2-(2-Chloro-phenyl)-5,7-dihydroxy-8-(2-hydroxymethyl-1-methyl-pyrrolidin-3-yl)-chromen-4-one hydrochloride The compound was prepared by the method as disclosed in example 15 of published US application US20070015802, and example 10 of published PCT application, WO2007148158.

Example 8

(+)-trans-2-(2-Bromo-5-fluoro-phenyl)-5,7-dihydroxy-8-(2-hydroxymethyl-1-methyl-pyrrolidin-3-yl)-chromen-4-one The compound was prepared by the method as disclosed in example 140 of published US application US20070015802, and example 15 of published PCT application, WO2007148158.

Example 9

(+)-trans-2-(2-Bromo-5-fluoro-phenyl)-5,7-dihydroxy-8-(2-hydroxymethyl-1-methyl-pyrrolidin-3-yl)-chromen-4-one hydrochloride The compound was prepared by the method as disclosed in example 16 of published PCT application, WO2007148158.

Example 10

(+)-trans-2-(2-Bromo-5-fluoro-phenyl)-5,7-dihydroxy-8-(2-hydroxymethyl-1-methyl-pyrrolidin-3-yl)-chromen-4-one methane sulfonate The compound was prepared by the method as disclosed in example 17 of published PCT application, WO2007148158.

Example 11

(+)-trans-2-(2-Chloro-4-cyano-phenyl)-5,7-dihydroxy-8-(2-hydroxymethyl-1-methyl-pyrrolidin-3-yl)-chromen-4-one The compound was prepared by the method as disclosed in example 39 of published PCT application, WO2007148158.

Example 12

(+)-trans-2-(2-Chloro-4-cyano-phenyl)-5,7-dihydroxy-8-(2-hydroxymethyl-1-methyl-pyrrolidin-3-yl)-chromen-4-one hydrochloride The compound was prepared by the method as disclosed in example 40 of published PCT application, WO2007148158.

Example 13

(+)-trans-2-(4-Bromo-2-chloro-phenyl)-5,7-dihydroxy-8-(2-hydroxymethyl-1-methyl-pyrrolidin-3-yl)-chromen-4-one The compound was prepared by the method as disclosed in example 100 of published US application US20070015802, and example 34 of published PCT application, WO2007148158.

Example 14

(+)-trans-2-(4-Bromo-2-chloro-phenyl)-5,7-dihydroxy-8-(2-hydroxymethyl-1-methyl-pyrrolidin-3-yl)-chromen-4-one hydrochloride The compound was prepared by the method as disclosed in example 35 of published PCT application, WO2007148158.

Example 15

(+)-trans-2-(2-Bromo-4-nitro-phenyl)-5,7-dihydroxy-8-(2-hydroxymethyl-1-methyl-pyrrolidin-3-yl)-chromen-4-one The compound was prepared by the method as disclosed in example 42 of published US application US20070015802

Example 16

(+)-trans-2-(2-Bromo-4-nitro-phenyl)-5,7-dihydroxy-8-(2-hydroxymethyl-1-methyl-pyrrolidin-3-yl)-chromen-4-one hydrochloride The compound was prepared by the method as disclosed in example 43 of published US application US20070015802.

Example 17

(+)-trans-2-(2,4-Dichloro-phenyl)-5,7-dihydroxy-8-(2-hydroxymethyl-1-methyl-pyrrolidin-3-yl)-chromen-4-one The compound was prepared by the method as disclosed in example 30 of published POT application, WO2007148158.

Example 18

(+)-trans-2-(2,4-Dichloro-phenyl)-5,7-dihydroxy-8-(2-hydroxymethyl-1-methyl-pyrrolidin-3-yl)-chromen-4-one hydrochloride The compound was prepared by the method as disclosed in example 31 of published PCT application, WO2007148158.

Example 19

(+)-trans-2-(2-Chloro-5-fluoro-phenyl)-5,7-dihydroxy-8-(2-hydroxymethyl-1-methyl-pyrrolidin-3-yl)-chromen-4-one The compound was prepared by the method as disclosed in example 27 of published US application US20070015802.

Example 20

(+)-trans-2-(2-Chloro-5-fluoro-phenyl)-5,7-dihydroxy-8-(2-hydroxymethyl-1-methyl-pyrrolidin-3-yl)-chromen-4-one hydrochloride The compound was prepared by the method as disclosed in example 28 of published US application US20070015802.

Example 21

(+)-trans-5,7-Dihydroxy-8-(2-hydroxymethyl-1-methyl-pyrrolidin-3-yl)-2-thiophen-2-yl-chromen-4-one The compound was prepared by the method as disclosed in example 68 of published US application US20070015802.

Example 22

(+)-trans-5,7-Dihydroxy-8-(2-hydroxymethyl-1-methyl-pyrrolidin-3-yl)-2-thiophen-2-yl-chromen-4-one hydrochloride The compound was prepared by the method as disclosed in example 69 of published US application US20070015802.

Example 23

(+)-trans-3-Nitro-benzoic acid 2-(2-acetoxymethyl-1-methyl-pyrrolidin-3-yl)-6-acetyl-3,5-dimethoxy-phenyl ester 3-nitrobenzoic acid (1.42 g, 8.49 mmol) was converted to its acid chloride using oxalyl chloride (0.998 mL, 11.38 mmol). Triethylamine (1.586 mL, 11.38 mmol) was added to a solution of compound of example 1 (2.0 g, 5.69 mmol) in dry DCM (20 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Yield: 2.6 g (61.25%).

Example 24

(+)-trans-8-(2-Hydroxymethyl-1-methyl-pyrrolidin-3-yl)-5,7-dimethoxy-2-(3-nitro-phenyl)-chromen-4-one To a solution of n-BuLi (15% solution in hexane, 5.32 mL, 12.48 mmol) in THF (30 mL), maintained at 0° C. under nitrogen atmosphere, hexamethyldisilazane (2.63 mL, 12.48 mmol) was added dropwise and stirred for 15 minutes. To this, a solution of compound of example 23 (2.5 g, 4.97 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to yield trans-acetic acid 3-{2-hydroxy-4,6-dimethoxy-3-[3-(3-nitro-phenyl)-3-oxo-propionyl]-phenyl}-1-methyl-pyrrolidin-2-ylmethyl ester as an oil (2.2 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to afford the title compound.

Yield: 1.15 g (52.51%); $^1$H NMR ($CDCl_3$, 300 MHz): δ 8.81 (t, 1H), 8.45 (d, 1H), 8.35 (d, 1H), 7.58 (t, 1H), 6.76 (s, 1H), 6.47 (s, 1H), 4.50 (m, 1H), 4.01 (s, 3H), 4.02 (s, 3H), 3.81 (dd, 1H), 3.41 (m, 2H), 2.90 (m, 2H), 2.55 (s, 3H), 2.19 (m, 2H); MS (ES+): m/z 441 (M+1).

Example 25

(+)-trans-5,7-dihydroxy-8-(2-hydroxymethyl-1-methyl-pyrrolidin-3-yl)-2-(3-nitrophenyl)-chromen-4-one A mixture of compound of example 24 (0.5 g, 1.13 mmol) and pyridine hydrochloride (1.2 g, 10.38 mmol) was heated at 180° C. for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.250 g (53.53%); $^1$H NMR ($CDCl_3$, 300 MHz): δ 12.44 (s, 1H), 8.86 (s, 1H), 8.38 (d, 1H), 8.15 (d, 1H), 7.72 (t, 1H), 6.67 (s, 1H), 6.31 (s, 1H), 4.39 (dd, 1H), 4.07 (dd, 1H), 3.86 (m, 1H), 3.33 (m, 2H), 2.85 (m, 1H), 2.66 (s, 3H), 2.56 (m, 1H), 2.01 (m, 1H); MS (ES+): m/z 413 (M+1).

Example 26

(+)-trans-5,7-dihydroxy-8-(2-hydroxymethyl-1-methyl-pyrrolidin-3-yl)-2-(3-nitrophenyl)-chromen-4-one hydrochloride The compound of example 25 (0.225 g, 0.545 mmol) was suspended in methanol (2 mL) and treated with ethereal HCl and the organic solvent was evaporated to afford the title salt.

Yield: 0.225 g (92.21%); $^1$H NMR (DMSO-$d_6$, 300 MHz): δ 12.87 (s, 1H), 11.63 (s, 1H), 8.81 (s, 1H), 8.55 (d, 1H), 8.42 (d, 1H), 7.85 (1, 1H), 7.22 (s, 1H), 6.47 (s, 1H), 4.15 (m, 1H), 3.69 (m, 5H), 2.92 (s, 3H), 2.42 (m, 1H), 2.22 (m, 1H).

MS (ES+): m/z 413 (M+1) (corresponding to freebase).

Example 27

(+)-trans 3-Bromo-2-chloro-benzoic acid 2-acetyl-6-(2-hydroxymethyl-1-methyl-pyrrolidin-3-yl)-3,5-dimethoxy-phenyl ester 3-Bromo-2-chloro-benzoic acid (2.0 g, 8.53 mmol) was converted to its acid chloride using oxalyl chloride (0.99 mL, 11.3 mmol). Triethylamine (1.586 mL, 11.3 mmol) was added to a solution of compound of example 1 (2.0 g, 5.69 mmol) in dry DCM (15 mL). To this, a solution of the acid chloride dissolved in dry DCM (10 mL) was added drop wise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Yield: 3.0 g (66.99%).

Example 28

(+)-trans-2-(3-Bromo-2-chloro-phenyl)-8-(2-hydroxymethyl-1-methyl-pyrrolidin-3-yl)-5,7-dimethoxy-chromen-4-one To a solution of n-BuLi (15% solution in hexane, 5.54 mL, 13.10 mmol) in THF (30 mL), maintained at 0° C. under nitrogen atmosphere, hexamethyldisilazane (2.764 mL, 13.10 mmol) was added drop wise and stirred for 15 minutes. To this, a solution of compound of example 27 (3.0 g, 5.27 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to yield acetic acid 3-{3-[3-(3-bromo-2-chloro-phenyl)-3-oxo-propionyl]-2-hydroxy-4,6-dimethoxy-phenyl}-1-methyl-pyrrolidin-2-ylmethyl ester as an oil (2.4 g, 4.21 mmol), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to afford the title compound.

Yield: 0.423 g (15.74%); $^1$H NMR ($CDCl_3$, 300 MHz): δ 7.81 (dd, 1H), 7.62 (dd, 1H), 7.34 (dd, 1H), 6.46 (s, 1H), 6.43 (s, 1H), 4.27 (m, 1H), 4.02 (s, 6H), 3.85 (m, 2H), 3.74 (m, 2H), 3.01 (m, 1H), 2.87 (s, 3H), 2.48 (m, 1H), 2.26 (m, 1H); MS (ES+): m/z 509 (M+1).

Example 29

(+)-trans-2-(3-Bromo-2-chloro-phenyl)-5,7-dihydroxy-8-(2-hydroxymethyl-1-methyl-pyrrolidin-3-yl)-chromen-4-one A mixture of compound of example 28 (0.280 g, 0.550 mmol) and pyridine hydrochloride (0.780 g, 6.74 mmol) was heated at 180° C. for a period of 2.5 hours. The reaction mixture was diluted with methanol (60 mL) and basified with solid Na$_2$CO$_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.125 g (47.34%); $^1$H NMR (CD3OD, 300 MHz): δ 7.92 (dd, 1H), 7.67 (dd, 1H), 7.40 (t, 1H), 6.32 (s, 1H), 6.13 (s, 1H), 3.93 (m, 1H), 3.74 (dd, 1H), 3.61 (dd, 1H), 3.44 (m, 1H), 3.27 (m, 1H), 3.07 (m, 1H), 2.71 (s, 3H), 2.20 (m, 2H); MS (ES+): m/z 480.

Example 30

(+)-trans-2-(3-Bromo-2-chloro-phenyl)-5,7-dihydroxy-8-(2-hydroxymethyl-1-methyl-pyrrolidin-3-yl)-chromen-4-one hydrochloride The compound of example 29 (0.120 g, 0.24 mmol) was suspended in methanol (2 mL) and treated with ethereal HCl and the organic solvent was evaporated to afford the title salt.
Yield: 0.120 (93.02%)

Example 31

(+)-trans-3-Chloro-benzoic acid 2-(2-acetoxymethyl-1-methyl-pyrrolidin-3-yl)-6-acetyl-3,5-dimethoxy-phenyl ester 3-chlorobenzoic acid (1.15 g, 7.39 mmol) was converted to its acid chloride using thionylchloride (0.81 mL, 10.9 mmol). Triethylamine (3.85 mL, 27.7 mmol) was added to a solution of compound of example 1 (2.0 g, 5.69 mmol) in dry DCM (15 mL). To this, a solution of the acid chloride dissolved in dry DCM (5.0 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.
Yield: 3.8 g (100%).

Example 32

(+)-trans-2-(3-Chloro-phenyl)-8-(2-hydroxymethyl-1-methyl-pyrrolidin-3-yl)-5,7-dimethoxy-chromen-4-one To a solution of n-BuLi (15% solution in hexane, 8.2 mL, 19.25 mmol) in THF (30 mL), maintained at 0° C. under nitrogen atmosphere, hexamethyldisilazane (4.06 mL, 19.9 mmol) was added drop wise and stirred for 15 minutes. To this, a solution of compound of example 31 (3.8 g, 7.75 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous Na$_2$SO$_4$. The organic layer was concentrated under reduced pressure and dried under vacuum to obtain acetic acid 3-{3-[3-(3-chloro-phenyl)-3-oxo-propionyl]-2-hydroxy-4,6-dimethoxy-phenyl}-1-methyl-pyrrolidin-2-ylmethyl ester as an oil (2.7 g), which was dissolved in conc. HCl (60 mL) and stirred for 3 hours to effect cyclisation. At the end of 3 hours, the reaction mixture was basified with solid NaHCO$_3$ to pH 8-9. The aqueous layer was extracted with chloroform (50×3 mL) and washed with water (25 mL) and brine (25 mL). The organic layer was dried over anhydrous Na$_2$SO$_4$, concentrated under reduced pressure and dried over vacuum. The residue was purified by column chromatography with 3% methanol in chloroform and 0.01% ammonia as eluent to afford the title compound.

Yield: 0.565 g (16.95%); $^1$H NMR (CDCl$_3$, 300 MHz): δ 8.02 (d, 1H), 7.82 (d, 1H), 7.42 (t, 2H), 6.6 (s, 1H), 6.42 (s, 1H), 4.32 (m, 1H), 3.97 (s, 3H), 3.95 (s, 3H), 3.78 (d, 1H), 3.25 (m, 2H), 2.75 (m, 2H), 2.55 (m, 2H), 2.40 (s, 3H); MS (ES+): m/z 431.1 (M+1).

Example 33

(+)-trans-2-(3-Chloro-phenyl)-5,7-dihydroxy-8-(2-hydroxymethyl-1-methyl-pyrrolidin-3-yl)-chromen-4-one A mixture of compound of example 32 (0.565 g, 1.31 mmol) and pyridine hydrochloride (1.2 g, 10.38 mmol) was heated at 180° C. for a period of 2.5 hours. The reaction mixture was diluted with methanol (60 mL) and basified with solid Na$_2$CO$_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.150 g (19.96%); $^1$H NMR (CD$_3$OD, 300 MHz): δ 7.83 (d, 1H), 7.71 (d, 1H), 7.49 (d, 1H), 7.43 (t, 1H), 6.53 (s, 1H), 6.28 (s, 1H), 4.31 (m, 1H), 4.05 (d, 1H), 3.82 (m, 1H), 3.31 (m, 2H), 2.85 (m, 3H), 2.66 (s, 3H); 2.53 (m, 1H),
2.01 (m, 1H); MS (ES+): m/z 402.1 (M+1).

Example 34

(+)-trans-2-(3-Chloro-phenyl)-5,7-dihydroxy-8-(2-hydroxymethyl-1-methyl-pyrrolidin-3-yl)-chromen-4-one hydrochloride The compound of example 33 (0.140 g, 0.349 mmol) was suspended in methanol (2 mL) and treated with ethereal HCl and the organic solvent was evaporated to afford the title compound, the hydrochloride salt.
Yield: 0.100 g (65.40%)

Example 35

(+)-trans-2-Chloro-3-nitro-benzoic acid 2-(2-acetoxymethyl-1-methyl-pyrrolidin-3-yl)-6-acetyl-3,5-dimethoxy-phenyl ester 2-chloro-3-nitro-benzoic acid (1.5 g, 7.44 mmol) was converted to its acid chloride using oxalyl chloride (0.83 mL, 9.9.45 mmol). Triethylamine (2.80 mL, 20.19 mmol) was added to a solution of compound of example 1 in dry DCM (15 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.
Crude yield: 3.8 g.

Example 36

(+)-trans-2-(2-Chloro-3-nitro-phenyl)-8-(2-(hydroxymethyl)-1-methyl-pyrrolidin-3-yl)-5,7-dimethoxy-chromen-4-one To a solution of n-BuLi (15% solution in hexane, 8.2 mL, 19.25 mmol) in THF (30 mL), maintained at 0° C. under nitrogen atmosphere, hexamethyldisilazane (4.02 mL, 19.25 mmol) was added drop wise and stirred for 15 minutes. To this, a solution of compound of example 35 (3.8 g, 7.11 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to yield acetic acid 3-{3-[3-(2-chloro-3-nitro-phenyl)-3-oxo-propionyl]-2-hydroxy-4,6-dimethoxy-phenyl}-1-methyl-pyrrolidin-2-ylmethyl ester as an oil (2.5 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$ concentrated under reduced pressure and dried over vacuum. The residue was purified by column chromatography with 3% methanol in chloroform and 0.01% ammonia as eluent to afford the title compound.

Yield: 0.90 g (26.59%); $^1$H NMR ($CDCl_3$, 300 MHz): δ 7.93 (dd, 1H), 7.87 (dd, 1H), 7.54 (t, 1H), 6.48 (s, 1H), 6.43 (s, 1H), 4.11 (m, 1H), 3.978 (s, 3H), 3.94 (s, 3H), 3.63 (m, 1H), 3.29 (m, 2H), 2.65 (m, 1H), 2.47 (m, 2H), 2.29 (s, 3H), 2.01 (m, 1H); MS (ES+): m/z 475.1 (M+1).

Example 37

(+)-trans-2-(2-Chloro-3-nitro-phenyl)-5,7-dihydroxy-8-(2-hydroxymethyl-1-methyl-pyrrolidin-3-yl)-chromen-4-one A mixture of compound of example 36 (0.900 g, 1.88 mmol) and pyridine hydrochloride (0.600 g, 5.1 mmol) was heated at 180° C. for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.300 g (35.6%); $^1$H NMR (DMSO-d6, 300 MHz): δ 8.26 (dd, 1H), 8.07 (dd 1H), 7.77 (t, 1H), 6.56 (s, 1H), 6.11 (s, 1H), 3.72 (m, 1H), 3.47 (d, 2H), 2.86 (m, 2H), 2.71 (m, 1H), 2.41 (s, 3H), 2.11 (m, 1H); 2.79 (m, 1H); MS (ES+): m/z 447.1 (M+1); MS (ES−): m/z 445.1 (M−1).

Example 38

(+)-trans-2-(2-Chloro-3-nitro-phenyl)-5,7-dihydroxy-8-(2-hydroxymethyl-1-methyl-pyrrolidin-3-yl)-chromen-4-one hydrochloride The compound of example 37 (0.250 g, 0.560 mmol) was suspended in methanol (2 mL) and treated with ethereal HCl and the organic solvent was evaporated to afford the title compound, the hydrochloride salt.

Yield: 0.200 g (74.01%)

Example 39

(+)-trans-2-Chloro-3-trifluoromethyl-benzoic acid 2-(2-acetoxymethyl-1-methyl-pyrrolidin-3-yl)-6-acetyl-3,5-dimethoxy-phenyl ester 2-Chloro-3-trifluoromethyl-benzoic acid (10.0 g, 44.5 mmol) was converted to its acid chloride using oxalyl chloride (4.6 mL, 50.7 mmol). Triethylamine (7.2 mL, 52.0 mmol) was added to a solution of compound of example 1 (13.6 g, 38.70 mmol) in dry DCM (60 mL). To this, a solution of the acid chloride dissolved in dry DCM (10.0 mL) was added drop wise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Crude yield: 25.0 g.

Example 40

(+)-trans-2-(2-Chloro-3-trifluoromethyl-phenyl)-8-(2-hydroxymethyl-1-methyl-pyrrolidin-3-yl)-5,7-dimethoxy-chromen-4-one To a solution of n-BuLi (15% solution in hexane, 4.2 mL, 9.8 mmol) in THF (30 mL), maintained at 0° C. under nitrogen atmosphere, hexamethyldisilazane (2.06 mL, 9.8 mmol) was added drop wise and stirred for 15 minutes. To this, a solution of compound of example 39 (2.2 g, 3.9 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to yield acetic acid 3-{3-[3-(2-chloro-3-trifluoromethyl-phenyl)-3-oxo-propionyl]-2-hydroxy-4,6-dimethoxy-phenyl}-1-methyl-pyrrolidin-2-ylmethyl ester as an oil (2.0 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to afford the title compound.

Yield: 0.560 g (28.89%); $^1$H NMR (MeOD, 300 MHz): δ 8.05 (d, 1H), 7.99 (d, 1H), 7.72 (dd, 1H), 6.74 (s, 1H), 6.41 (s, 1H), 4.04 (s, 3H), 4.01 (s, 3H), 3.86 (m, 1H), 3.53 (m, 2H), 3.33 (m, 1H), 2.99 (t, 1H), 2.75 (t, 1H), 2.36 (s, 3H), 2.08 (m, 2H).

Example 41

(+)-trans-2-(2-Chloro-3-trifluoromethyl-phenyl)-5,7-dihydroxy-8-(2-hydroxymethyl-1-methyl-pyrrolidin-3-yl)-chromen-4-one A mixture of compound of example 40 (0.560 g, 1.12 mmol) and pyridine hydrochloride (0.700 g, 6.05 mmol) was heated at 180° C. for a period of 2.5 hours. The reaction mixture was diluted with methanol (60 mL) and basified with solid Na$_2$CO$_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.100 g (18.96%); $^1$H NMR (CD$_3$OD, 300 MHz): δ 8.04 (d, 1H), 7.98 (dd, 1H), 7.70 (t, 1H), 6.37 (s 1H), 6.14 (s, 1H), 3.93 (m, 1H), 3.72 (d, 1H), 3.62 (d, 1H), 3.33 (m, 1H), 2.68 (s, 3H), 2.62 (m, 2H); 2.19 (m, 2H); MS (ES–): m/z 468 (M–1).

Example 42

(+)-trans-2-(2-Chloro-3-trifluoromethyl-phenyl)-5,7-dihydroxy-8-(2-hydroxymethyl-1-methyl-pyrrolidin-3-yl)-chromen-4-one hydrochloride The compound of example 41 (0.090 g, 0.192 mmol) was suspended in methanol (1.5 mL) and treated with ethereal HCl and the organic solvent was evaporated to afford the title compound, the hydrochloride salt.

Yield: 0.085 g (87.58%)

Example 43

(+)-trans-2-Chloro-3-methyl-benzoic acid 2-(2-acetoxymethyl-1-methyl-pyrrolidin-3-yl)-6-acetyl-3,5-dimethoxy-phenyl ester 2-Chloro-3-methyl-benzoic acid (1.42 g, 8.3 mmol) was converted to its acid chloride using oxalyl chloride (0.893 mL, 10.0 mmol). Triethylamine (1.37 mL, 9.6 mmol) was added to a solution of compound of example 1 (2.26 g, 6.4 mmol) in dry DCM (15 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Crude yield: 3.0 g.

Example 44

(+)-trans-2-(2-Chloro-3-methyl-phenyl)-8-(2-hydroxymethyl-1-methyl-pyrrolidin-3-yl)-5,7-dimethoxy-chromen-4-one NaH (0.840 g, 29.7 mmol) was suspended in dry DMF (15 mL) and a solution of compound of example 43 (3.0 g, 5.95 mmol) in 15 mL of dry DMF was added dropwise. Reaction was stirred at room temperature in nitrogen atmosphere for 2 hours. The reaction mixture was quenched with methanol (1.0 mL). Ammonium chloride solution was added to it followed by extraction in DCM (3×20 mL) and the solvent removed under reduced pressure to obtain acetic acid 3-{3-[3-(2-chloro-3-methyl-phenyl)-3-oxo-propionyl]-2-hydroxy-4,6-dimethoxy-phenyl}-1-methyl-pyrrolidin-2-ylmethyl ester as an oil (2.5 g, 5.6 mmol), which was dissolved in conc. HCl (15 mL) and stirred for 3 hours to effect cyclisation. At the end of 3 hours, the reaction mixture was basified with solid NaHCO$_3$ to pH 8-9. The aqueous layer was extracted with chloroform (20×3 mL) and washed with water (20 mL) and brine (20 mL). The organic layer was dried over anhydrous Na$_2$SO$_4$, concentrated under reduced pressure and dried over vacuum.

The residue was purified by column chromatography with 3% methanol in chloroform and 0.01% ammonia as eluent to afford the title compound.

Yield: 1.5 g (56.9%); $^1$H NMR (CDCl$_3$, 300 MHz): δ 7.37 (dd, 1H), 7.24 (t, 1H), 6.39 (s, 1H), 6.10 (s, 2H), 3.92 (s, 3H), 3.84 (m, 1H), 3.76 (s, 6H), 3.55 (d, 1H), 3.33 (m, 1H), 3.19 (m, 1H), 2.69 (m, 1H), 2.58 (m, 2H), 2.37 (s, 3H), 2.20 (m, 1H); MS (ES+): m/z 444.2 (M+1).

Example 45

(+)-trans-2-(2-Chloro-3-methyl-phenyl)-5,7-dihydroxy-8-(2-hydroxymethyl-1-methyl-pyrrolidin-3-yl)-chromen-4-one A mixture of compound of example 44 (1.0 g, 2.25 mmol) and pyridine hydrochloride (3.0 g, 25.95 mmol) was heated at 180° C. for a period of 2.5 hours. The reaction mixture was diluted with methanol (60 mL) and basified with solid Na$_2$CO$_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.300 g (32.12%); $^1$H NMR (DMSO-d$_6$ 300 MHz): δ 7.58 (d, 1H), 7.56 (d 1H), 7.41 (t, 1H), 6.41 (s, 1H), 6.13 (s, 1H), 3.71 (m, 1H), 3.40 (m, 2H), 2.79 (m, 2H), 2.40 (m, 1H), 2.41 (s, 3H), 2.39 (m, 3H), 2.10 (m, 1H), 1.78 (m, 1H); MS (ES+): m/z 416 (M+1).

Example 46

(+)-trans-2-(2-Chloro-3-methyl-phenyl)-5,7-dihydroxy-8-(2-hydroxymethyl-1-methyl-pyrrolidin-3-yl)-chromen-4-one hydrochloride The compound of example 45 (0.300 g, 0.72 mmol) was suspended in methanol (1.5 mL) and treated with ethereal HCl and the organic solvent was evaporated to afford the title compound, the hydrochloride salt.

Yield: 0.250 g (76.9%)

Example 47

(+)-trans-2-Chloro-3-pyrrolidin-1-yl-benzoic acid 2-(2-acetoxymethyl-1-methyl-pyrrolidin-3-yl)-6-acetyl-3,5-dimethoxy-phenyl ester 2-Chloro-3-pyrrolidin-1-yl-benzoic acid (1.6 g, 7.15 mmol) was converted to its acid chloride using thionyl chloride (0.79 mL, 10.7 mmol). Triethylamine (1.13 mL, 8.5 mmol) was added to a solution of compound of example 1 (2.0 g, 5.6 mmol) in dry DCM (15 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Yield: 3.5 g (84.87%)

Example 48

(+)-trans-(2-Chloro-3-pyrrolidin-1-yl-phenyl)-8-(2-hydroxymethyl-1-methyl-pyrrolidin-3-yl)-5,7-dimethoxy-chromen-4-one To a solution of n-BuLi (15% solution in hexane, 6.85 mL, 15.6 mmol) in THF (30 mL), maintained at 0° C. under nitrogen atmosphere, hexamethyldisilazane (3.36 mL, 15.6 mmol) was added drop wise and stirred for 15 minutes. To this, a solution of compound of example 47 (3.5 g, 6.4 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to obtain acetic acid 3-{3-[3-(2-chloro-3-pyrrolidin-1-yl-phenyl)-3-oxo-propionyl]-2-hydroxy-4,6-dimethoxy-phenyl}-1-methyl-pyrrolidin-2-ylmethyl ester as an oil (4.0 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to afford the title compound.

Yield: 0.650 g (22.96%); $^1$H NMR ($CDCl_3$, 300 MHz): 7.23 (d, 1H), 7.03 (dd, 2H), 6.46 (s, 1H), 6.36 (s, 1H), 4.02 (s, 3H), 3.97 (s, 3H), 3.91 (dd, 2H), 3.8 (dd, 2H), 3.63 (m, 1H), 3.40 (m, 4H), 3.05 (dd, 2H), 2.82 (m, 1H). 2.62 (dd, 1H), 2.46 (m, 2H), 2.24 (s, 3H), 1.96 (m, 1H); MS (ES+): m/z 499.2 (M+1).

Example 49

(+)-trans-2-(2-Chloro-3-pyrrolidin-1-yl-phenyl)-5,7-dihydroxy-8-(2-hydroxymethyl-1-methyl-pyrrolidin-3-yl)-chromen-4-one A mixture of compound of example 48 (0.650 g, 1.30 mmol) and pyridine hydrochloride (1.5 g, 12.90 mmol) was heated at 180° C. for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to yield the title compound as a yellow solid.

Yield: 0.075 g (12.0%); $^1$H NMR ($CD_3OD$, 300 MHz): δ 7.32 (d, 1H), 7.10 (d, 1H), 7.09 (d, 1H), 6.98 (s, 1H), 6.62 (s, 1H), 4.97 (m, 1H), 4.25 (m, 1H), 3.90 (t, 2H), 3.34 (s, 2H), 2.90 (m, 2H), 2.50 (s, 3H), 2.10 (s, 4H), 1.33 (s, 4H); MS (ES+): m/z 471.2 (M+1).

Example 50

(+)-trans-2-(2-Chloro-3-pyrrolidin-1-yl-phenyl)-5,7-dihydroxy-8-(2-hydroxymethyl-1-methyl-pyrrolidin-3-yl)-chromen-4-one hydrochloride The compound of example 49 (0.075 g, 0.159 mmol) was suspended in methanol (1 mL) and treated with ethereal HCl and the organic solvent was evaporated to afford the title compound, the hydrochloride salt.

Yield: 0.070 g (86.92%)

Example 51

(+)-trans-3-Bromo-benzoic acid 2-(2-acetoxymethyl-1-methyl-pyrrolidin-3-yl)-6-acetyl-3,5-dimethoxy-phenyl ester 3-bromobenzoic acid (1.37 g, 6.8 mmol) was converted to its acid chloride using oxalyl chloride (0.76 mL, 8.8 mmol). Triethylamine (4.04 mL, 28 mmol) was added to a solution of compound of example 1 (2.0 g, 5.69 mmol) in dry DCM (20 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Crude yield: 4.6 g

Example 52

(+)-trans-2-(3-Bromo-phenyl)-8-(2-hydroxymethyl-1-methyl-pyrrolidin-3-yl)-5,7-dimethoxy-chromen-4-one To a solution of n-BuLi (15% solution in hexane, 9.18 mL, 21.5 mmol) in THF (30 mL), maintained at 0° C. under nitrogen atmosphere, hexamethyldisilazane (4.51 mL, 21.4 mmol) was added dropwise and stirred for 15 minutes. To this, a solution of compound of example 51 (4.6 g, 8.6 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to obtain acetic acid 3-{3-[3-(3-bromo-phenyl)-3-oxo-propionyl]-2-hydroxy-4,6-dimethoxy-phenyl}-1-methyl-pyrrolidin-2-ylmethyl ester as an oil (5.0 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to afford the title compound.

Yield: 1.4 g (35.3%); $^1$H NMR ($CDCl_3$, 300 MHz): δ 9.21 (d, 1H), 8.90 (d, 1H), 8.70 (d, 1H), 8.48 (t, 1H), 7.72 (s, 1H), 7.53 (s, 1H) 5.65 (m, 1H), 4.14 (s, 3H), 4.09 (s, 3H), 4.69 (m, 2H), 4.33 (m, 2H), 4.18 (m, 2H), 3.88 (s, 3H), 3.36 (m, 2H); MS (ES+): m/z 474.0 (M+1).

Example 53

(+)-trans-2-(3-Bromo-phenyl)-8-(2-hydroxymethyl-1-methyl-pyrrolidin-3-yl)-5,7-dihydroxy-chromen-4-one A mixture of compound of example 52 (1.40 g, 3.04 mmol) and pyridine hydrochloride (2.0 g, 17.30 mmol) was heated at 180° C. for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.540 g (39.4%); $^1$H NMR ($CDCl_3$, 300 MHz): δ 8.04 (t, 1H), 7.78 (d, 1H), 7.65 (d, 1H), 7.39 (,m, 1H), 6.56 (s, 1H), 6.30 (s, 1H), 4.32 (dd, 1H), 4.03 (dd, 1H), 3.84 (dd, 1H), 3.32 (m, 2H), 2.91 (m, 1H), 2.68 (s, 3H), 2.55 (m, 2H), MS (ES+): m/z 447.68 (M+1).

Example 54

(+)-trans-2-(3-Bromo-phenyl)-8-(2-hydroxymethyl-1-methyl-pyrrolidin-3-yl)-5,7-dihydroxy-chromen-4-one hydrochloride The compound of example 53 (0.540 g, 1.2099 mmol) was suspended in methanol (2 mL) and treated with ethereal HCl and the organic solvent was evaporated to afford the title compound, the hydrochloride salt.

Yield: 0.500 g (85.64%)

Example 55

(+)-trans-2,3-Dichloro-benzoic acid 2-(2-acetoxymethyl-1-methyl-pyrrolidin-3-yl)-6-acetyl-3,5-dimethoxy-phenyl ester 2,3-dichloro benzoic acid (1.3 g, 6.82 mmol) was converted to its acid chloride using oxalyl chloride (0.76 mL, 8.87 mmol). Triethylamine (4.04 mL, 28 mmol) was added to a solution of compound of example 1 (2.0 g, 5.69 mmol) in dry DCM (20 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Crude yield: 4.35 g

Example 56

(+)-trans-2-(2,3-Dichloro-phenyl)-8-(2-hydroxymethyl-1-methyl-pyrrolidin-3-yl)-5,7-dimethoxy-chromen-4-one To a solution of n-BuLi (15% solution in hexane, 8.15 mL, 19.1 mmol) in THF (30 mL), maintained at 0° C. under nitrogen atmosphere, hexamethyldisilazane (4.0 mL, 19.1 mmol) was added dropwise and stirred for 15 minutes. To this, a solution of compound of example 55 (4.35 g, 8.29 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to obtain acetic acid 3-{3-[3-(2,3-dichloro-phenyl)-3-oxo-propionyl]-2-hydroxy-4,6-dimethoxy-phenyl}-1-methyl-pyrrolidin-2-ylmethyl ester as an oil (4.5 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$ concentrated under reduced pressure and dried over vacuum. The residue was purified by column chromatography with 3% methanol in chloroform and 0.01% ammonia as eluent to afford the title compound.

Yield: 0.670 (25.47%); $^1$H NMR ($CD_3OD$, 300 MHz): δ 8.77 (d, 1H), 8.66 (d, 1H), 8.55 (t, 1H), 7.51 (s, 1H), 7.56 (s, 1H), 5.37 (m, 2H), 5.13 (s, 3H), 5.11 (s, 3H). 4.95 (m, 1H), 4.83 (dd, 3H), 4.70 (m, 2H), 3.37 (d, 1H), 3.84 (s, 3H), 3.47 (m, 2H); MS (ES+): m/z 464.1 (M+1).

Example 57

(+)-trans-2-(2,3-Dichloro-phenyl)-5,7-dihydroxy-8-(2-hydroxymethyl-1-methyl-pyrrolidin-3-yl)-chromen-4-one A mixture of compound of example 56 (0.670 g, 1.44 mmol) and pyridine hydrochloride (2.0 g, 17.30 mmol) was heated at 180° C. for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.310 g (49.34%); $^1$H NMR (DMSO-d6, 300 MHz): δ 77.78 (d, 1H), 7.71 (d, 1H), 7.49 (m, 1H), 6.52 (s, 1H), 6.38 (s, 1H), 4.21 (m, 1H), 3.87 (m, 2H), 3.68 (m, 1H), 3.60 (dd, 1H), 3.37 (m, 1H), 2.97 (s, 3H), 2.51 (m, 1H), 2.27 (m, 1H); MS (ES−): m/z 434.1 (M−1).

Example 58

(+)-trans-2-(2,3-Dichloro-phenyl)-5,7-dihydroxy-8-(2-hydroxymethyl-1-methyl-pyrrolidin-3-yl)-chromen-4-one hydrochloride The compound of example 57 (0.310 g, 0.714 mmol) was suspended in methanol (1.5 mL) and treated with ethereal HCl and the organic solvent was evaporated to afford the title compound, the hydrochloride salt.

Yield: 0.300 g (89.11%)

Example 59

(+)-trans-2-Chloro-3-iodo-benzoic acid 2-(2-acetoxymethyl-1-methyl-pyrrolidin-3-yl)-6-acetyl-3,5-dimethoxy-phenyl ester 2-Chloro-3-iodo-benzoic acid (1.92 g, 6.8 mmol) was converted to its acid chloride using oxalyl chloride (0.76 mL, 8.8 mmol). Triethylamine (4.04, 28 mmol) was added to a solution of compound of example 1 (2.0 g, 5.69 mmol) in dry DCM (20 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Crude yield: 5.2 g.

Example 60

(+)-trans-2-(2-Chloro-3-iodo-phenyl)-8-(2-hydroxymethyl-1-methyl-pyrrolidin-3-yl)-5,7-dimethoxy-chromen-4-one To a solution of n-BuLi (15% solution in hexane, 9.01 mL, 21.0 mmol) in THF (30 mL), maintained at 0° C. under nitrogen atmosphere, hexamethyldisilazane (4.44 mL, 21.0 mmol) was added dropwise and stirred for 15 minutes. To this, a solution of compound of example 59 (5.2 g, 8.4 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to obtain acetic acid 3-{3-[3-(2-chloro-3-iodo-phenyl)-3-oxo-propionyl]-2-hydroxy-4,6-dimethoxy-phenyl}-1-methyl-pyrrolidin-2-ylmethyl ester as an oil (4.8 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$ concentrated under reduced pressure and dried over vacuum. The residue was purified by column chromatography with 3% methanol in chloroform and 0.01% ammonia as eluent to afford the title compound.

Yield: 0.430 g (9.15%); $^1$H NMR ($CDCl_3$, 300 MHz): δ 8.04 (d, 1H), 7.63 (d, 1H), 7.14 (t, 1H), 6.40 (s, 1H), 6.47 (s, 1H), 4.19 (m, 1H), 4.02 (s, 3H), 4.01 (s, 3H), 3.89 (d, 1H), 3.50 (m, 2H), 2.95 (m, 2H), 2.56 (s, 3H), 2.25 (m, 2H).

Example 61

(+)-trans-2-(2-Chloro-3-iodo-phenyl)-5,7-dihydroxy-8-(2-hydroxymethyl-1-methyl-pyrrolidin-3-yl)-chromen-4-one A mixture of compound of example 60 (0.430 g, 0.77 mmol) and pyridine hydrochloride (2.0 g, 17.30 mmol) was heated at 180° C. for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.120 g (29.4%); $^1$H NMR ($CD_3OD$, 300 MHz): δ 8.15 (d, 1H), 7.68 (d, 1H), 7.23 (t, 1H), 6.30 (s, 1H), 6.15 (s, 1H), 3.94 (m, 1H), 3.78 (d, 2H), 3.41 (m, 2H), 3.05 (m, 1H), 2.71 (s, 3H), 2.20 (m, 2H); MS (ES+): m/z 528.0 (M+1); MS (ES−): m/z 526.02 (M−1).

Example 62

(+)-trans-2-(2-Chloro-3-iodo-phenyl)-5,7-dihydroxy-8-(2-hydroxymethyl-1-methyl-pyrrolidin-3-yl)-chromen-4-one hydrochloride The compound of example 61 (0.120 g, 0.227 mmol) was suspended in methanol (1 mL) and treated with ethereal HCl and the organic solvent was evaporated to afford the title compound, the hydrochloride salt.

Yield: 0.115 g (89.90%)

Example 63

(+)-trans-2-Chloro-3-isopropylamino-benzoic acid 2-(2-acetoxymethyl-1-methyl-pyrrolidin-3-yl)-6-acetyl-3,5-dimethoxy-phenyl ester 2-Chloro-3-isopropylamino-benzoic acid (1.8 g, 8.19 mmol) was converted to its acid chloride using oxalyl chloride (0.80 g, 9.0 mmol). Triethylamine (1.87 ml, 18.5 mmol) was added to a solution of compound of example 1 (2.4 g, 6.8 mmol) in dry DCM (20 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.

Crude yield: 3.0 g.

Example 64

(+)-trans-2-(2-Chloro-3-isopropylamino-phenyl)-8-(2-hydroxymethyl-1-methyl-pyrrolidin-3-yl)-5,7-dimethoxy-chromen-4-one To a solution of n-BuLi (15% solution in hexane, 5.85 mL, 13.7 mmol) in THF (30 mL), maintained at 0° C. under nitrogen atmosphere, hexamethyldisilazane (2.87 mL, 13.7 mmol) was added dropwise and stirred for 15 minutes. To this, a solution of compound of example 63 (3.0 g, 5.4 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to obtain acetic acid 3-{3-[3-(2-chloro-3-isopropylamino-phenyl)-3-oxo-propionyl]-2-hydroxy-4,6-dimethoxy-phenyl}-1-methyl-pyrrolidin-2-ylmethyl ester as an oil (3.0 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$ concentrated under reduced pressure and dried over vacuum. The residue was purified by column chromatography with 3% methanol in chloroform and 0.01% ammonia as eluent to afford the title compound.

Yield: 1.0 g (37.5%); $^1$H NMR ($CDCl_3$, 300 MHz): δ 7.50 (d, 1H), 7.67 (d, 1H), 6.40 (s, 1H), 6.10 (s, 1H), 5.95 (s, 1H), 3.94 (m, 1H), 3.87 (s, 3H), 3.89 (s, 3H), 3.56 (m, 2H), 3.43 (m, 1H), 3.23 (m, 2H), 2.75 (m, 2H), 2.57 (s, 3H); 2.46 (s, 3H), 2.44 (s, 3H); MS (ES+): m/z 487.2 (M+1).

Example 65

(+)-trans-2-(2-Chloro-3-isopropylamino-phenyl)-5,7-dihydroxy-8-(2-hydroxy methyl-1-methyl-pyrrolidin-3-yl)-chromen-4-one A mixture of example 64 (0.900 g, 1.98 mmol) and pyridine hydrochloride (2.0 g, 17.30 mmol) was heated at 180° C.

for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.070 g (8.08%); $^1$H NMR ($CD_3OD$, 300 MHz): δ 7.73 (d, 1H), 7.05 (d, 1H), 6.91 (d, 1H), 6.58 (s, 1H), 6.37 (s, 1H), 7.72 (d, 1H), 7.05 (d, 1H), 6.93 (d, 1H), 6.58 (s, 1H), 6.37 (s, 1H), 4.39 (m, 1H), 4.15 (m, 1H), 3.98 (m, 1H), 3.58 (m, 1H), 2.65 (m, 2H), 3.50 (m, 2H), 2.37 (m, 1H), 3.03 (s, 3H), 1.30-1.28 (d, 6H); MS (ES+): m/z 459.2 (M+1); MS (ES−): m/z 457.2 (M−1).

Example 66

(+)-trans-2-(2-Chloro-3-isopropylamino-phenyl)-5,7-dihydroxy-8-(2-hydroxy methyl-1-methyl-pyrrolidin-3-yl)-chromen-4-one hydrochloride The compound of example 65 (0.070 g, 0.153 mmol) was suspended in methanol (1 mL) and treated with ethereal HCl and the organic solvent was evaporated to afford the title compound, the hydrochloride salt.
Yield: 0.065 g (85.91%)

Example 67

(+)-trans-3-Iodo-benzoic acid 2-(2-acetoxymethyl-1-methyl-pyrrolidin-3-yl)-6-acetyl-3,5-dimethoxy-phenyl ester 3-Iodo-benzoic acid (1.83 g, 7.37 mmol) was converted to its acid chloride using oxalyl chloride (0.98 mL, 11.06 mmol), triethylamine (1.52 mL, 11.06 mmol) was added to a solution of compound of example 1 (2.0 g, 5.69 mmol) in dry DCM (20 mL). To this, a solution of the acid chloride dissolved in dry DCM (10 mL) was added dropwise and the reaction stirred at 25° C. for 2 hours. The reaction mixture was poured over crushed ice, basified with saturated sodium carbonate solution (pH 10), extracted with chloroform (3×200 mL), and the solvent removed under reduced pressure to afford the title compound as a viscous oil.
Crude yield: 4.6 g.

Example 68

(+)-trans-2-(3-Iodo-phenyl)-8-(2-hydroxymethyl-1-methyl-pyrrolidin-3-yl)-5,7-dimethoxy-chromen-4-one To a solution of n-BuLi (15% solution in hexane, 8.4 mL, 19.77 mmol) in THF (30 mL), maintained at 0° C. under nitrogen atmosphere, hexamethyldisilazane (4.14 mL, 19.77 mmol) was added dropwise and stirred for 15 minutes. To this, a solution of compound of example 67 (4.6 g, 7.9 mmol) in THF (30 mL) was added drop wise, maintaining the temperature at 0° C. After the addition, the reaction was allowed to warm to room temperature and stirred for 2.5 hours. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous $Na_2SO_4$. The organic layer was concentrated under reduced pressure and dried under vacuum to obtain acetic acid 3-{3-[3-(3-iodophenyl)-3-oxo-propionyl]-2-hydroxy-4,6-dimethoxy-phenyl}-1-methyl-pyrrolidin-2-ylmethyl ester as an oil (5.0 g), which was dissolved in conc. HCl (60 mL) and stirred for 3 hours to effect cyclisation. At the end of 3 hours, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to afford the title compound.

Yield: 0.6 g (14.5%); $^1$H NMR ($CDCl_3$, 300 MHz): δ 8.39 (d, 1H), 7.97 (d, 1H), 7.85 (d, 1H), 7.25 (t, 1H), 6.65 (d, 1H), 6.48 (s, 1H), 4.46 (m, 1H), 4.10 (s, 3H), 4.07 (s, 3H), 3.94 (d, 1H), 3.47 (m, 2H), 2.95 (m, 2H), 2.60 (s, 3H), 2.23 (m, 2H).

Example 69

(+)-trans-2-(3-Iodo-phenyl)-5,7-dihydroxy-8-(2-hydroxymethyl-1-methyl-pyrrolidin-3-yl)-chromen-4-one A mixture of compound of example 68 (0.4 g, 0.70 mmol) and pyridine hydrochloride (0.327 g, 2.83 mmol) was heated at 180° C. for a period of 2.5 hours. The reaction mixture was diluted with methanol (60 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to afford the title compound.

Yield: 0.15 g (42.97%); $^1$H NMR ($CD_3OD$, 300 MHz): δ 8.38 (d, 1H), 8.02 (d, 1H), 7.94 (d, 1H), 733 (t, 1H), 6.65 (s, 1H), 6.15 (s, 1H), 4.25 (m, 1H), 3.75 (d, 2H), 3.42 (m, 2H), 3.33 (m, 1H), 2.80 (s, 3H), 2.35 (m, 2H); MS (ES+): m/z 494.21 (M+1).

Example 70

(+)-trans-2-(3-Iodo-phenyl)-5,7-dihydroxy-8-(2-hydroxymethyl-1-methyl-pyrrolidin-3-yl)-chromen-4-one hydrochloride The compound of example 69 (0.050 g, 0.101 mmol) was suspended in methanol (1 mL) and treated with ethereal HCl and the organic solvent was evaporated to afford the title salt.
Yield: 0.045 g (84.14%).

Biological Screening of Compounds:

The efficacy of the compounds of formula 1 in inhibiting inflammatory cytokines comprising Tumor Necrosis Factor-alpha (TNF-α) and interleukins (IL-1β, IL-6, IL-8), and/or inhibiting the expression of cell adhesion molecules comprising intercellular adhesion molecule1 (ICAM-1), vascular-cell adhesion molecule1 (VCAM-1) and E-Selectin can be determined by a number of pharmacological assays well known in the art. The exemplified pharmacological assays, which follow, have been carried out with the compounds of formula 1 and/or their salts.

Assays

Example 71

In Vitro Screening to Identify Inhibitors of TNF-α, IL-1β, IL-6 and IL-8

Cytokine production by lipopolysaccharides (LPS) in hPBMCs (human peripheral blood mononuclear cells) was measured as in reference, Physiol. Res. 2003, 52, 593-598, the disclosure of which is incorporated by reference for the teaching of the assay.

Blood was collected from healthy donors into Potassium EDTA vacutainer tubes (BID vacutainer). The PBMC were isolated using gradient centrifugation in Histopaque-1077 solution (Sigma). Isolated PBMC were suspended in RPMI 1640 (Rosewell Park Memorial Institute) culture medium (Sigma-Aldrich Fine Chemicals, USA) containing 10% fetal bovine serum (FBS) (JRH, USA), 100 U/mL penicillin (Sigma Chemical Co. St Louis, Mo., USA) and 100 µg/mL streptomycin (Sigma Chemical Co. St Louis, Mo.). The cell concentration was adjusted to $1 \times 10^6$ cells/mL. The viability as determined by trypan blue dye exclusion was uniform Ly≥98%. The cell suspension (100 µL) was added to the wells of a 96-well culture plate. Following cell plating, 79 µL of the culture medium and 1 µL of various concentrations of test compounds (compounds of formula 1) (final concentration 0.001, 0.003, 0.005, 0.01, 0.025, 0.03, 0.05, 0.1, 0.25, 0.3 and 1 µM) dissolved in DMSO (dimethyl sulfoxide, Sigma, Mo., USA) were added to the cells. The final concentration of DMSO was adjusted to 0.5%. The vehicle (0.5% DMSO) was used as control. Rolipram (300 µM), a PDE4-selective inhibitor (synthesized in Medicinal Chemistry Department, Piramal Life Sciences Limited (PLSL)), was used as a standard TNF-α inhibitor, whereas SB 203580 (an inhibitor of p38 mitogen-activated protein (MAP) kinase) (10 µM) (Sigma) was used as a standard for IL-1β (interleukin-1beta), IL-6 (interleukin-6), and IL-8 (interleukin-8) inhibition. The plates were incubated for 30 minutes at 37° C. in an atmosphere of 5% $CO_2$. Finally, 20 µL (10 µg/mL) per well of LPS, (*Escherchia coli* 0127:B8, Sigma Chemical Co., St. Louis, Mo.) was added to the wells of the incubated plates, for a final concentration of 1 µg/mL. The plates were incubated at 37° C. for 5 hours in an atmosphere of 5% $CO_2$. To assess the cytotoxic effect of the compounds of formula 1, the cellular viability test was performed using MTS (3-(4,5-dimethylthiazol-2-yl)-5-(3-carboxymethoxyphenyl)-2-(4-sulfonyl)-2H-tetrazolium) reagent after 5 hours of incubation. Supernatants were harvested and assayed for TNF-α, IL-1β, IL-6 and IL-8 by ELISA as described by the manufacturer. (OptiEIA ELISA sets, BD Biosciences, Pharmingen). The 50% inhibitory concentration ($IC_{50}$) values were calculated by a nonlinear regression method using GraphPad software (Prism 3.03).

The following Table(s) 1 and 1A show(s) results of the above experiments.

TABLE 1

$IC_{50}$ values for inhibition of TNF-α

| Test Compounds | Activity (TNF-α) $IC_{50}$ µM |
|---|---|
| Compound of example 3 | 1.0 |
| Compound of example 5 | 0.4 |
| Compound of example 7 | 0.2 |
| Compound of example 9 | 0.9 |
| Compound of example 12 | 1.5 |
| Compound of example 16 | 0.3 |
| Compound of example 18 | 0.3 |
| Compound of example 20 | 0.7 |
| Compound of example 22 | 2.3 |
| Compound of example 26 | 0.4 |
| Compound of example 30 | 4.1 |
| Compound of example 34 | 2.5 |
| Compound of example 38 | 1.3 |
| Compound of example 42 | 2.4 |
| Compound of example 46 | 0.5 |
| Compound of example 58 | 1.5 |

TABLE 1-continued $IC_{50}$ values for inhibition of TNF-α

| Test Compounds | Activity (TNF-α) $IC_{50}$ µM |
|---|---|
| Compound of example 62 | 1.3 |
| Compound of example 66 | 0.9 |

TABLE 1A $IC_{50}$ values of representative compound, compound of example 3, for inhibition of LPS-induced TNF-α, IL-1β, IL-6 and IL-8 release from hPBMCs

| Test Compound(s) | $IC_{50}$ (µM) | | | |
|---|---|---|---|---|
| | TNF-α | IL-1β | IL-6 | IL-8 |
| Compound of example 3 | 1.0 | 0.1 | 0.1 | 1.3 |

Based on the above data it can be seen that the compound of example 3, a representative compound of formula 1, effectively blocked the expression of proinflammatory cytokines (TNF-α, IL-1β, IL-6 and IL-8) by LPS-stimulated freshly isolated human peripheral blood mononuclear cells.

Example 72

In Vitro Screening Method to Identify Inhibitors of TNF-α Release

Synovial Tissue Setup

Cytokine production in synovial cells obtained from rheumatoid arthritis patients undergoing knee replacement surgery, was measured as per the method described in reference, Lancet, 1989, 29, 244-247, the disclosure of which is incorporated herein by reference for the teaching of the assay.

The synovial membrane tissue was digested by incubating at 37° C. for 3 hours in an atmosphere of 5% $CO_2$, in Roswell Park Memorial Institute (RPMI) medium containing penicillin-G (100 U/mL), streptomycin (100 µg/mL), amphotericin B (50 ng/mL) (GIBCO), 1.33 mg/mL collagenase Type I (Worthington Biochemical Corporation, New Jersey, USA), 0.5 µg/mL DNAse Type I (SIGMA) and 8.33 U/mL heparin (Biological E. Limited, India). The digested tissue was then filtered through a membrane (mesh size 70 micron) (SIGMA), the cells were washed 3 times and suspended in complete medium (RPMI supplemented with 5% FCS and 5% human serum). The cell concentration was adjusted to $1 \times 10^6$ cells/mL. The viability as determined by trypan blue dye exclusion was uniform Ly≥98%. The cell suspension (100 µL) was added to the wells of a 96-well culture plate. Following cell plating, 100 µL of the culture medium and 1 µL of various concentrations of the compound of example 3 (final concentration 0.001, 0.003, 0.01, 0.03, 0.1, 0.3, 1 and 3 µM) dissolved in DMSO (dimethylsulfoxide, Sigma, Mo., USA) were added to the cells. The final concentration of DMSO was adjusted to 0.5%. The vehicle (0.5° A) DMSO) was used as control. SB 203580 (20 µM) was used as a standard. The plates were incubated for 16 hours at 37° C. in 5% $CO_2$ atmosphere. The culture plates were centrifuged (2,500 rpm for 10 minutes) and the supernatants collected and stored at −70° C. The amount of TNF-α, Interleukin-β (IL-1β), Interleukin-6 (IL-6) and Interleukin-8 (IL-8) in the supernatants were assayed using the ELISA protocol recommended by the manufacturers (OptiEIA ELISA sets, BD Bio- Sciences Pharmingen). The 50% inhibitory concentration ($IC_{50}$) values were calculated by a nonlinear regression method using the GraphPad software (Prism 3.03).

The following Table 2 shows results of the above experiment.

TABLE 2

$IC_{50}$ values of representative compound, compound of example 3, for inhibition of spontaneous release of TNF-α, IL-6 and IL-8 from freshly isolated cells obtained from RA patients

| Test compound(s) | $IC_{50}$ (μM) | | |
|---|---|---|---|
| | TNF-α | IL-6 | IL-8 |
| Compound of example 3 | 20 | 10 | 3.5 |

Based on the above data it can be seen that the compound of example 3, a representative compound of formula 1, blocked the expression of proinflammatory cytokines (TNF-α, IL-6 and IL-8) in freshly isolated synovial cells.

Example 73

In Vitro Screening to Identify Inhibitors of Adhesion Molecule Expression

The assay was designed as in reference, Transplantation, 1997, 63(5), 759-764, the disclosure of which is incorporated herein by reference for the teaching of the assay.

Human umbilical vein endothelial cells (HUVECs) were obtained from Cascade Biologics (Oregon-USA). Cells were cultured in M-200 medium (Cascade Biologics) supplemented with low serum growth supplements (LSGS) (Cascade Biologics), penicillin-G (100 U/mL), streptomycin (100 μg/mL) and amphotericin B (50 ng/mL) (GIBCO). Confluent HUVECs in 96-well fibronectin-coated plates were pretreated with various concentrations of the compound of example 3 (final concentration 0.003, 0.005, 0.01, 0.025, 0.05, 0.1, 0.3 and 1 μM) dissolved in DMSO (dimethylsulfoxide, Sigma, Mo., USA). The final concentration of DMSO was adjusted to 0.5%. The vehicle (0.5% DMSO) was used as control. BAY 11-7082 (inhibitor of cytokine-induced IκB-α phosphorylation)(0.5 and 1 μM) (Calbiochem) was used as a standard inhibitor of endothelial cell adhesion molecule (ECAMs) expression. The plates were incubated at 37° C. in an atmosphere of 5% $CO_2$. After TNF-α stimulation (1 ng/mL) (R&D Systems (Minneapolis, Minn.)) for 4 hours at 37° C. in an atmosphere of 5% $CO_2$, supernatants were harvested and assayed for the expression of ICAM-1 (intercellular cell adhesion molecules), whereas the expressions of VCAM-1 (vascular cell adhesion molecules) and E-selectin were evaluated after 6 hours of stimulation. To assess the cytotoxic effect of the compound, the cellular viability test was performed using MTS (3-(4,5-dimethylthiazol-2-yl)-5-(3-carboxymethoxyphenyl)-2-(4-sulfonyl)-2H-tetrazolium) reagent. To quantitatively measure the amount of cell surface expressions of ICAM-1, VCAM-1 and E-selectin, ELISA assay was performed using anti-ICAM-1 (clone BBIG-I1), anti-VCAM-1 (clone BBIG-V1), anti-E-selectin (clone BBIG-E4) antibodies, isotype control mouse $IgG_1$ (clone 11711.11) and the secondary antibody (anti-mouse IgG-HRP antibody) which were procured from R&D Systems (Minneapolis, Minn., USA). The 50% inhibitory concentration ($IC_{50}$) values were calculated by a nonlinear regression method using GraphPad software (Prism 3.03)

The results of this study are presented in the following Table 3.

TABLE 3

$IC_{50}$ values of representative compound, compound of example 3, for inhibition of TNF-α induced cell surface expression of ICAM-1, V-CAM-1 and E-selectin on HUVECs

| Test compound(s) | $IC_{50}$ (μM) | | |
|---|---|---|---|
| | ICAM-1 | VCAM-1 | E-selectin |
| Compound of example 3 | 0.67 | 0.28 | 0.65 |

Based on the results presented in the above Table 3, it can be seen that the compound of example 3, a representative compound of formula 1, effectively blocked the expression of endothelial cell adhesion molecules ICAM-1, VCAM-1 and E-selectin, in TNF-α stimulated HUVEC (n=2).

Example 74

In Vitro Screening for p38 MAP Kinase Inhibition and IκBα Degradation

The method for identifying inhibitors of p38 mitogen-activated protein (MAP) Kinase was designed as in reference, Journal of Lipid Research, 1999, 40, 1911-1919, the disclosure of which is incorporated herein by reference for teaching of the assay.

The method for IκBα degradation was designed as in reference, The Journal of Immunology, 1999, 103, 6800-6809, the disclosure of which is also incorporated by reference for the teaching of the assay.

Materials

Human Jurkat T-cells from American Type Culture Collection (ATCC) were cultivated in Rosewell Park Memorial Institute (RPMI) medium supplemented with 10% fetal bovine serum (FBS), penicillin (100 U/mL) and streptomycin (100 μg/mL) at 37° C. in humidified atmosphere of 95% air-5% $CO_2$. Culture medium was changed every 2-3 days and always 24 hours before harvest. RPMI medium, FBS, CellLytic, anti-β-actin, sodium orthovanadate and anisomycin were purchased from Sigma-Aldrich (USA). TNF-α was purchased from R & D Systems (USA). Complete Protease inhibitor cocktail was procured from Roche.

Methods

Preparation of Cytoplasmic Extracts for Western Blotting

Jurkat cells were preincubated with vehicle or the compound of example 3 (0.1 μM) for 1 hour in a 37° C., $CO_2$ incubator. For MAPK experiments, the cells were stimulated with anisomycin (10 μg/mL) for 30 minutes. SB 203580 was used as a standard (1 μM). For studies pertaining to degradation of IκBα and IκBα (phospho) the cells were stimulated with 0.1 nM TNF-α for 0, 5, 15, 30, 60 and 90 minutes. The cells were harvested, rapidly washed with ice-cold PBS and lysed with cold CellLytic buffer supplemented with complete protease inhibitor cocktail and sodium orthovanadate. The protein extracts were obtained after centrifugation at 15,000 rpm at 4° C. (20 minutes). Aliquots of the resulting extracts were analyzed for their protein content using the Coomassie Plus Protein Assay Reagent (Pierce) following manufacturer's instructions.

Western Blotting

Primary antibodies were as follows:

p38 MAPK, phospho-p38 MAPK, IκBα and phospho-IκBα were purchased from Calbiochem (USA). Anti-β-actin was bought from Sigma (USA).

In all the experiments, equivalent amounts of protein (10 µg) was loaded on SDS/12.5%-polyacrylamide electrophoresis gels and resolved at 150 V for 2 hours in a buffered solution (24.9 mM Tris base, 250 mM glycine, 0.1% SDS (sodium dodecyl sulfate)). After electrophoresis, the proteins were transferred from the gel to a nitrocellulose membrane (Sigma-Aldrich) at 25 V for 45 minutes in transfer buffer (47.9 mM Tris base, 38.6 mM glycine, 0.037% SDS, 20% methanol; pH 9.2-9.4). Blots were blocked in Tris-buffered saline (TBS) (20 mM Tris base, 0.9% NaCl; pH 7.4) containing 5% nonfat dry milk (Santa Cruz Biotechnology) for 1 hour 15 minutes at room temperature, and incubated with the primary antibody which was prepared in SuperBlock Blocking Buffer in TBS (Pierce) at 4° C. overnight with gentle rocking. Membranes were washed and then probed with horse-radish peroxidase (HRP)-conjugated secondary antibody. Bands were visualized using chemiluminescent peroxidase substrate (Sigma-Aldrich) and a Kodak Imaging station. Blots were stripped with stripping buffer (50 mM Tris-HCl pH 6.8, 1% SDS and 100 mM β-mercaptoethanol) for 20 minutes at 50° C., washed and reprobed with a primary antibody to the housekeeping protein☐ β-actin as a loading control.

The results of this study are depicted in FIG. 1.

Based on the results of the above experiment, it can be said that the compound of example 3, a representative compound of formula 1, blocks TNFα-induced IkBα phosphorylation and degradation but is not an inhibitor of p38 MAP kinase Example 75

In Vitro Screening: PDE4 Inhibition

Human histiocytic lymphoma (U937) cells from the American Type Culture Collection were grown in plastic flasks in Roswell Park Memorial Institute 1640 culture medium (RPMI, Gibco BRL, UK) supplemented with 10% heat inactivated fetal calf serum (FBS), penicillin (100 U/mL) and streptomycin (100 µg/mL) at 37° C. in humidified atmosphere of 95% air-5% $CO_2$. Culture medium was changed every 2-3 days and always 24 hours before harvest. RPMI medium, FBS and Salbutamol were purchased from Sigma-Aldrich (USA). Rolipram was synthesized in the Medicinal Chemistry Department, Piramal Life Sciences Limited.

Method

In all the experiments, culture medium was removed by centrifugation (216×g for 5 minutes) and the cells were suspended in Krebs-Ringer-Henseleit buffer of the following composition (millimolar): sodium chloride (NaCl), 118; potassium chloride (KCl), 4.6; sodium bicarbonate ($NaHCO_3$), 24.9; (potassium dihydrogen phosphate ($KH_2PO_4$), 1; D-glucose, 11.1; calcium chloride ($CaCl_2$), 1; magnesium chloride ($MgCl_2$), 1.1; 4-(2-hydroxyethyl)-1-piperazineethanesulfonic acid, 5; (pH 7.4). To induce PDE4 activity, 490 µL aliquots of cells ($1.02\times10^6$ cells/mL) were preincubated with vehicle or various concentrations of the compound of example 3 (1, 3 and 10 µM) for 15 minutes in a 37° C. in humidified atmosphere of 95% air-5% $CO_2$, before being stimulated with salbutamol (1 µM) for 7 minutes. Rolipram was used as a standard (0.3, 1 and 3 µM). Salbutamol was dissolved in deionized water, the compound of example 3 and Rolipram, were dissolved in dimethyl sulfoxide (DMSO) and the final concentration of DMSO in the assay never exceeded 0.5% cAMP assay was performed using Bridge-It cAMP Designer Fluorescence Assay (Mediomics LLC, USA) in 96-well, black, flat-bottom plates, according to manufacturer's instructions. Fluorescence measurements were taken with Polarstar Optima (BMG Labtech-Germany).

Data Analysis

Relative fluorescence was calculated using the following formula where:

RF=Relative Fluorescence, $F_o$=fluorescent intensity of the blank or buffer control, F=fluorescence of cAMP or sample:

$RF=(F_o-F)/F_o$

Data was converted to RF values as presented in the following table 4. A standard curve was plotted using the RF values of the given standards and the values of cAMP corresponding to the test compounds were determined using the standard plot.

TABLE 4

Study of the effect of representative compound, compound of example 3, on PDE4 inhibition

| Compound | Concentration (µM) | Relative Fluorescence (RF) |
|---|---|---|
| Compound of example 3 | 1 | 0.71 |
|  | 3 | 0.95 |
|  | 10 | 0.95 |
| Rolipram | 0.3 | 1.39 |
|  | 1.0 | 1.56 |
|  | 3.0 | 1.73 |

From the results presented in the above table 4, it can be seen that the compound of example 3, a representative compound of formula 1, is not a PDE4 inhibitor.

Example 76

Induction of Apoptosis in Synovial Fluid Mononuclear Cells (SFMC)

The assay was designed as in reference, Arthritis and Rheumatism, Vol. 52, No. 1, January 2005, the disclosure of which is incorporated herein by reference for the teaching of the assay.

Synovial fluid was collected from rheumatoid arthritis patients under going knee aspiration. The fluid was collected in vacutainers and processed within 2 hours of collection. SFMC were isolated using gradient centrifugation using Ficoll-Hypaque solution (Sigma). Isolated SFMC were suspended in RPMI 1640 (Rosewell Park Memorial Institute) culture medium (Sigma-Aldrich Fine Chemicals, USA) containing 20% fetal bovine serum (FBS) (JRH, USA), 100 U/ml penicillin (Sigma Chemical Co. St Louis, Mo.) and 100 µg/mL streptomycin (Sigma Chemical Co. St Louis, Mo.). The cell concentration was adjusted to $1\times10^6$ cells/mL. The viability as determined by trypan blue dye exclusion was uniformly >98%. 4 mL of this cell suspension was added to each well of a 6-well plate. The SFMC were incubated for 3-4 hours. Non-adherent cells were removed and cultured separately in 6-well plates. Fresh medium was added to the adherent cells. After 24 hours incubation in a humidified atmosphere at 37° C. in 5% $CO_2$, non-adherent cells were removed and pooled with previous days samples. These cells were plated at a density of $2\times10^6$ cells/well. The adherent cell population was re-fed fresh complete medium. Following cell plating, both the adherent as well as non-adherent cell population were treated with 5 µM and 10 µM of compound of example 3, dissolved in DMSO (dimethylsulfoxide, Sigma, Mo., USA). The final concentration of DMSO was adjusted to 0.5%. The plates were incubated for 24 hours at 37° C. in a humidified atmosphere of 5% $CO_2$. The cells thus treated were harvested and stained with Annexin-V/Propidium iodide (AV/PI) to check for induction of apoptosis.

Harvesting and Staining of Cells

Cells were collected in 15 mL tubes. Adherent cells were dislodged by gentle scraping. After washing in PBS, the cell pellet was resuspended in 1× binding buffer (BD Pharmingen Cat#51-66121E). Cell count was adjusted to $1\times10^6$ cells/mL. 100 µL of this cell suspension was transferred to a FACS tube. 5 µL of Annexin-V was added followed by 5 µL of 50 µg/mL propidium iodide. This suspension was incubated in the dark for 15-20 minutes. The volume was made up with 400 µL binding buffer. Acquisition was done using a flow cytometer.

Figure 2A:
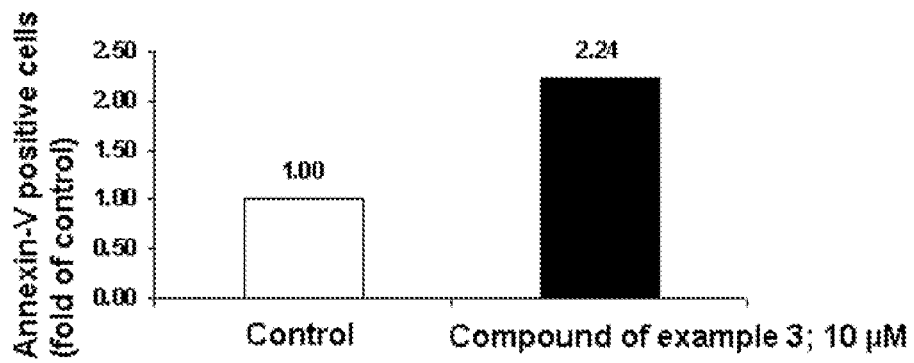
FIG. 2A shows the induction of apoptosis in adherent cell population of synovial fluid mononuclear cells (SFMC) by the representative compound, compound of IC) example 3
Figure 2B:
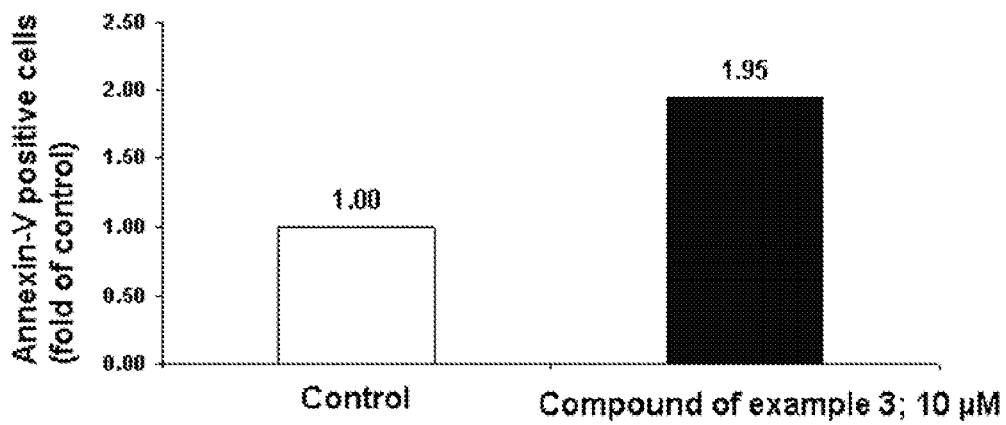
FIG. 2B shows the induction of apoptosis in non adherent cell population of synovial fluid mononuclear cells (SFMC) by the representative compound, compound of example 3

The results of the study are depicted in FIG. 2A and FIG. 2B.

Conclusion:

The compound of example 3 induces apoptosis in both adherent as well as non-adherent cell population of mononuclear cells isolated from synovial fluid acquired from rheumatoid arthritis patients.

Example 77

Anti-Arthritic Activity

Anti-arthritic potential of the compound of example 3, a representative compound of formula 1, was evaluated in vivo by using two different models.
1. LPS-induced TNF-α release in Balb/c mice.
2. Collagen-induced arthritis in mice.

A) LPS-Induced TNF-α Release in Balb/c Mice

The assay was designed as in reference, J. Med. Bio. Res., 1997, 30, 1199-1207, the disclosure of which is incorporated herein by reference for the teaching of the assay.

Protocol:

Balb/c mice (originally procured from National Institute of Nutrition, Hyderabad, India), of either sex weighing between 18-22 g were orally administered the compound of example 3 at doses of 12.5, 50, 75, 100 mg/kg. All suspensions were freshly prepared in 0.5% CMC. One hour later, LPS (1 mg/kg) (*Escherchia coli*, serotype 0127:B8, Sigma Chemical Co., St. Louis, Mo.) dissolved in sterile pyrogen-free saline was administered intra-peritoneally to the control group, standard treatment group (Rolipram, 30 mg/kg, p.o.) and test groups (compound of example 3), except the negative control group, which received normal saline.

Blood samples were collected from anesthetized mice, with heparin as an anti-coagulant (25 IU per sample) 1.5 hours post LPS challenge. These were then centrifuged at 10000 rpm for 10 minutes and plasma samples were analysed for levels of TNF-α by ELISA, as described by the manufacturer (OptiEIA ELISA sets, BD BioSciences Pharmingen).

Percent inhibition of TNF-α release was calculated by comparing the TNF-α levels of the treatment groups with those of the control group.

The results of this study are presented in the following Table 5.

TABLE 5

% Inhibition of LPS-induced TNF-α release in Balb/c mice for representative compound, compound of example 3

| Compound of example 3, mg/kg | % Inhibition of TNF-α release |
| --- | --- |
| 100 | 92.61 ± 3.5 |
| 75 | 77.34 ± 8.61 |
| 50 | 82.01 ± 4.88 |
| 25 | 66.8 ± 11.47 |
| 12.5 | 53.22 ± 12.49 |

It can be seen from the data presented in the above Table 5 that the compound of example 3, a representative compound of formula 1, inhibits LPS-induced TNF-α release in Balb/c mice in a dose-dependent manner.

B) Collagen Induced Arthritis in Mouse:

The assay was designed as in reference, J. Exp. Med., 1985, 162, 637-646, the disclosure of which is incorporated herein by reference for the teaching of the assay.

Protocol:

Male DBA/1J mice (originally procured from Jackson Laboratories, USA), aged 8-10 weeks were immunized with an emulsion equivalent to 200 µg of type II collagen in Freund's Complete Adjuvant, injected intradermally at the base of the tail. A booster shot with the same emulsion was given 21 days later. A group of naïve mice was maintained alongside.

From day 23 to day 56, mice were examined daily once for the signs of rheumatoid arthritis, using the Articular Index and paw thickness as parameters. Articular Index scoring was performed employing the following criteria:

Forelimbs: Scale 0-3
0: No redness or swelling
1: Redness, but no swelling
2: Redness and swelling of the paw
3: Redness and severe swelling of the paw Hind Limbs: Scale 0-5
0: No redness or swelling
1: Redness and mild swelling of paw
2: Redness and moderate swelling of paw and/or swelling of at least one of the digits.
3: Redness and moderate/severe swelling of paw, swelling of ankle joint and/or swelling of one or more digits.
4: Redness and severe swelling of paw, digits and ankle joint, with joint stiffness.
5: Redness and severe swelling of paw, digits and ankle joint, with joint stiffness and altered angle of digits.

Mice with a minimum hind paw score of 2 were inducted into the study.

Mice were randomized into the various study groups and orally administered the vehicle (0.5% CMC, 1 ml/kg), test compound (compound of example 3, 50 mg/kg twice daily) and standard compound (Enbrel, 3 mg/kg, s.c., once daily). Each group had a minimum of 8 mice. The dosing of the compounds was done for 23 days.

The following parameters were observed and recorded daily,
1. Body weight
2. Articular index
3. Paw thickness in mm using a tension free caliper 4. Any significant observation regarding the condition of the animal.

On the last day (24th day of dosing), one hour after the compound treatment, the animals were sacrificed, blood withdrawn, and plasma collected for drug level analyses. Also, the limbs of all the animals were preserved for histopathological evaluations.

Figure 3:
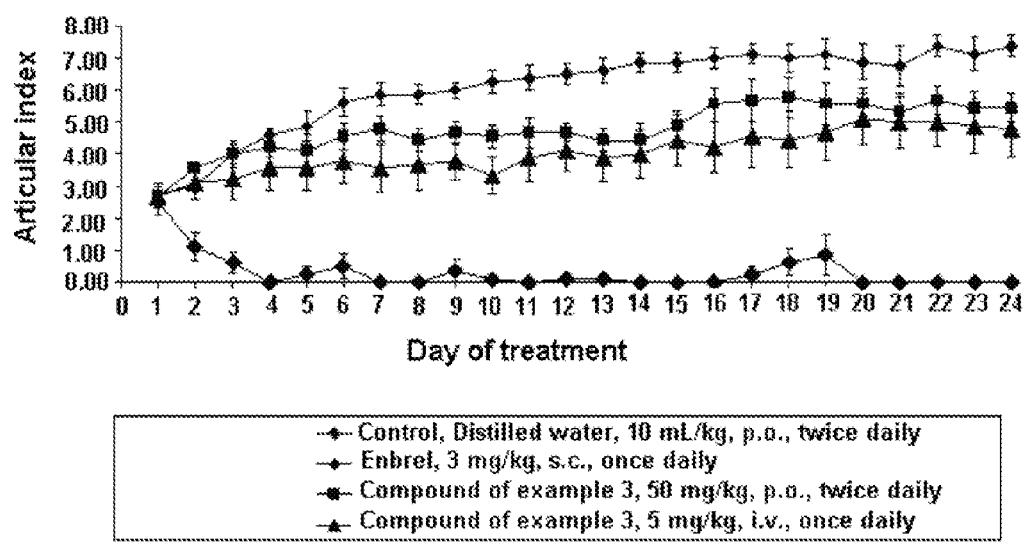
FIG. 3 shows the effect of treatment with representative compound, compound of example 3, on the articular index of sum of hind paws of arthritic (CIA)DBA/1J mice
Figure 4:
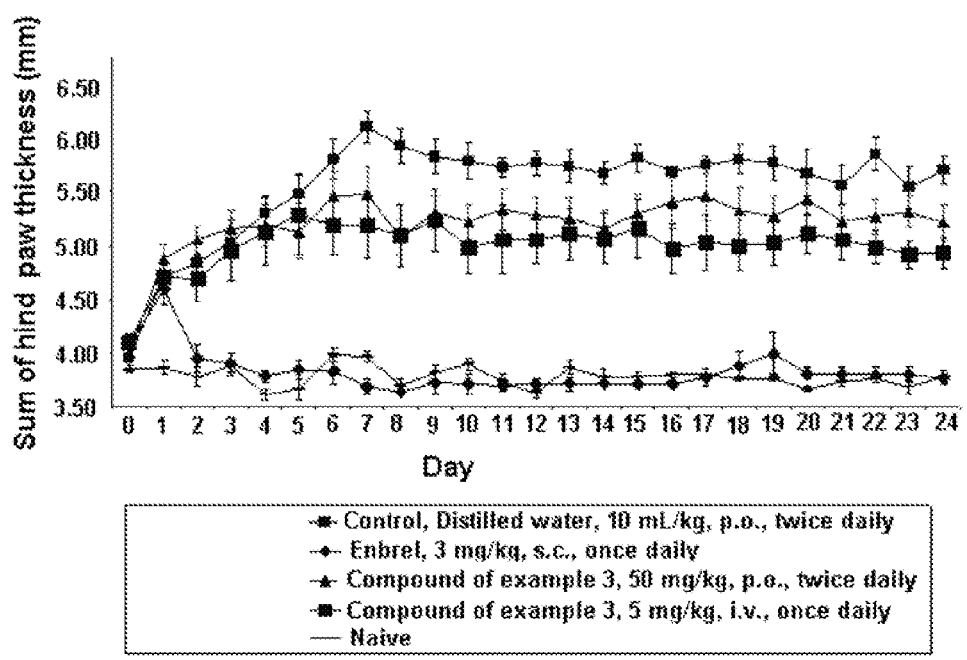
FIG. 4 shows the effect of treatment with representative compound, compound of example 3, on the paw thickness of arthritic (CIA)DBA/1J mice

The results are graphically depicted in FIG. 3 (Articular index versus days of treatment) and FIG. 4 (Paw thickness versus days of treatment). Data obtained during the course of this study (articular index and paw thickness) was statistically evaluated by applying Mann-Whitney U test.

Enbrel treated mice showed a significant reduction in the severity of the disease as assessed by articular index and paw thickness.

The compound of example 3, a representative compound of formula 1, also showed a trend towards ameriolation of the disease.

Histopathological Analysis:

Mice were humanely euthanized and the hind paws were harvested from each animal, fixed in 10% neutral buffered formalin, decalcified in 5% formic acid and embedded in paraffin. Section (μm) were stained with either hematoxylin and eosin or safranin 0 and evaluated microscopically. Histopathological changes were scored as follows: mild (score=1), moderate (score=2) or severe (score=3) for the parameters of cellular infiltration, bone erosions and cartilage damage, graded separately. Cartilage depletion was indicated visually by diminished safranin 0 staining of proteoglycan matrix. The mean total score was compared to that of vehicle treated group. In case of histological scoring, Kruskal-Wallis analysis was followed by Dunn's multiple comparison tests to evaluate the statistical difference between two groups. Values of p<0.05 were considered significant. Histological evaluation showed reduced joint inflammation, cartilage damage and bone destruction.

Figure 5:
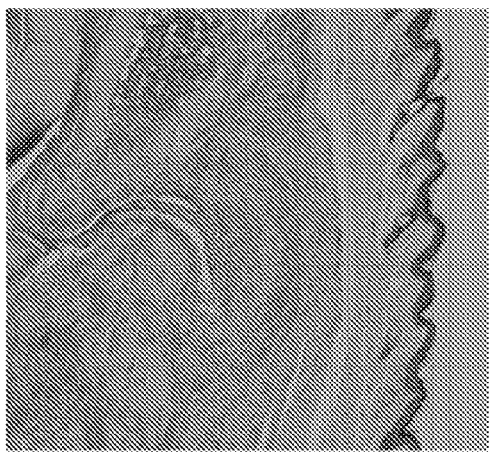
FIG. 5 shows the histopathological evaluation of animals treated with representative compound, compound of example 3 in comparison to vehicle (control) and Enbrel.
Figure 5:
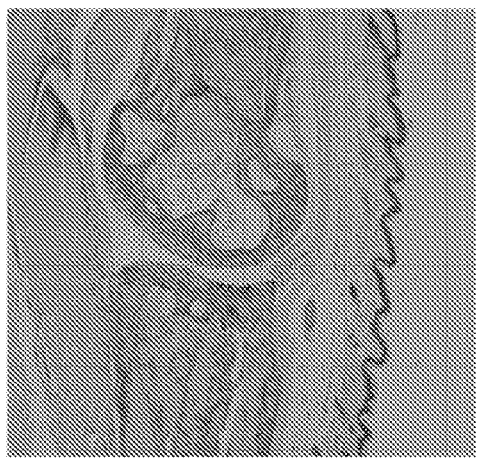
Figure 5:

The results of this experiment as shown in FIG. 5, indicated that the compound of example 3, a representative compound of formula 1, has a potential anti-arthritic effect.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method for the treatment of an inflammatory disorder comprising administering to a subject in need thereof a therapeutically effective amount of a compound of formula 1;

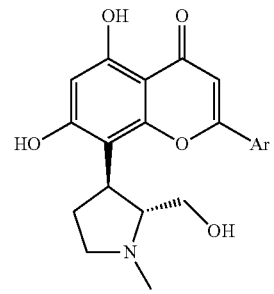

Formula 1 wherein

Ar is a phenyl ring, wherein the phenyl ring is substituted with 1 or 2 identical or different substituents selected from: halogen, nitro, cyano, $C_1$-$C_4$-alkyl, fluoromethyl, difluoromethyl, trifluoromethyl, hydroxyl, $C_1$-$C_4$ alkoxy, carboxy, and $NR_1R_2$;

wherein $R_1$ and $R_2$ are each independently selected from: hydrogen, $C_1$-$C_4$-alkyl, and $C_1$-$C_4$-alkylcarbonyl;

or a stereoisomer or a tautomer thereof, or a pharmaceutically acceptable salt thereof; wherein the inflammatory disorder is mediated by an inflammatory cytokine selected from the group consisting of tumor Necrosis Factor-alpha (TNF-α), interleukin-1 beta (IL-1β), interleukin-6 (IL-6) and interleukin-8 (IL-8), and the said inflammatory disorder is selected from the group consisting of rheumatoid arthritis, osteoarthritis, juvenile rheumatoid arthritis, psoriatic arthritis, osteoarthritis, refractory rheumatoid arthritis and chronic non-rheumatoid arthritis.

2. The method according to claim 1, wherein the compound of formula 1 is selected from:
- (+)-trans-2-(2-Chloro-4-trifluoromethyl-phenyl)-5,7-dihydroxy-8-(2-hydroxymethyl-1-methyl-pyrrolidin-3-yl)-chromen-4-one hydrochloride;
- (+)-trans-2-(2-Chloro-4-nitro-phenyl)-5,7-dihydroxy-8-(2-hydroxymethyl-1-methyl-pyrrolidin-3-yl)-chromen-4-one hydrochloride;
- (+)-trans-2-(2-Chloro-phenyl)-5,7-dihydroxy-8-(2-hydroxymethyl-1-methyl-pyrrolidin-3-yl)-chromen-4-one hydrochloride;
- (+)-trans-2-(2-Bromo-5-fluoro-phenyl)-5,7-dihydroxy-8-(2-hydroxymethyl-1-methyl-pyrrolidin-3-yl)-chromen-4-one hydrochloride;
- (+)-trans-2-(2-Chloro-4-cyano-phenyl)-5,7-dihydroxy-8-(2-hydroxymethyl-1-methyl-pyrrolidin-3-yl)-chromen-4-one hydrochloride;
- (+)-trans-2-(2-Bromo-4-nitro-phenyl)-5,7-dihydroxy-8-(2-hydroxymethyl-1-methyl-pyrrolidin-3-yl)-chromen-4-one hydrochloride;
- (+)-trans-2-(2,4-Dichloro-phenyl)-5,7-dihydroxy-8-(2-hydroxymethyl-1-methyl-pyrrolidin-3-yl)-chromen-4-one hydrochloride;
- (+)-trans-2-(2-Chloro-5-fluoro-phenyl)-5,7-dihydroxy-8-(2-hydroxymethyl-1-methyl-pyrrolidin-3-yl)-chromen-4-one hydrochloride;
- (+)-trans-5,7-dihydroxy-8-(2-hydroxymethyl-1-methyl-pyrrolidin-3-yl)-2-(3-nitrophenyl)-chromen-4-one hydrochloride;
- (+)-trans-2-(2-Chloro-3-nitro-phenyl)-5,7-dihydroxy-8-(2-hydroxymethyl-1-methyl-pyrrolidin-3-yl)-chromen-4-one hydrochloride;

(+)-trans-2-(2-Chloro-3-methyl-phenyl)-5,7-dihydroxy-8-(2-hydroxymethyl-1-methyl-pyrrolidin-3-yl)-chromen-4-one hydrochloride;

(+)-trans-2-(2,3-Dichloro-phenyl)-5,7-dihydroxy-8-(2-hydroxymethyl-1-methyl-pyrrolidin-3-yl)-chromen-4-one hydrochloride;

(+)-trans-2-(2-Chloro-3-iodo-phenyl)-5,7-dihydroxy-8-(2-hydroxymethyl-1-methyl-pyrrolidin-3-yl)-chromen-4-one hydrochloride; and (+)-trans-2-(2-Chloro-3-isopropylamino-phenyl)-5,7-dihydroxy-8-(2-hydroxymethyl-1-methyl-pyrrolidin-3-yl)-chromen-4-one hydrochloride.

* * * * *